United States Patent
Olesen et al.

(10) Patent No.: US 11,771,831 B2
(45) Date of Patent: Oct. 3, 2023

(54) AUTO INJECTOR WITH AUTOMATED RECONSTITUTION

(71) Applicant: Phillips-Medisize A/S, Struer (DK)

(72) Inventors: Jan Olesen, Holstebro (DK); Niels Skovby Rahbek, Holstebro (DK); Paul Erik Fabricius, Holstebro (DK)

(73) Assignee: Phillips-Medisize A/S, Struer (DK)

( * ) Notice: Subject to any disclaimer, the term of this patent is extended or adjusted under 35 U.S.C. 154(b) by 881 days.

(21) Appl. No.: 16/340,247

(22) PCT Filed: Sep. 7, 2017

(86) PCT No.: PCT/EP2017/072483
§ 371 (c)(1),
(2) Date: Apr. 8, 2019

(87) PCT Pub. No.: WO2018/068956
PCT Pub. Date: Apr. 19, 2018

(65) Prior Publication Data
US 2020/0038590 A1 Feb. 6, 2020

(30) Foreign Application Priority Data

Oct. 11, 2016 (DK) .............................. PA201600616

(51) Int. Cl.
*A61M 5/20* (2006.01)
(52) U.S. Cl.
CPC ... *A61M 5/2066* (2013.01); *A61M 2005/2006* (2013.01); *A61M 2005/2026* (2013.01)
(58) Field of Classification Search
CPC ........ A61M 5/2066; A61M 2005/2006; A61M 2005/2026; A61M 5/1409; A61M 5/1407;
(Continued)

(56) References Cited

U.S. PATENT DOCUMENTS

| 4,874,381 A | 10/1989 | Vetter |
| 5,711,782 A | 1/1998 | Okamura et al. |
(Continued)

FOREIGN PATENT DOCUMENTS

| AT | 14327 U1 | 8/2015 |
| CN | 103520806 A | 1/2014 |
(Continued)

OTHER PUBLICATIONS

International Search Report for PCT/EP2017/072483 dated Dec. 20, 2017.
(Continued)

*Primary Examiner* — Kevin C Sirmons
*Assistant Examiner* — Avery Smale

(57) ABSTRACT

Disclosed is an auto injector and a related method, and a related system, for administering injection of a medicament comprising a first medicament component and a second medicament component. The auto injector comprising a housing, a receiving part, an operational module and a processing unit. The processing unit being configured to operate a syringe operational part to move a carrier to mix the first medicament component and the second medicament component to obtain a mixed medicament. The movement of the carrier having a time varying acceleration profile. The time varying acceleration profile having a first maximum acceleration in a first mixing direction and a second maximum acceleration in a second mixing direction. The first maximum acceleration and/or the second maximum acceleration is larger than a predetermined acceleration threshold.

18 Claims, 11 Drawing Sheets

(58) Field of Classification Search
CPC .... A61M 5/19; A61M 5/20; A61M 2005/206;
A61M 2005/2073; A61M 5/2448; A61M
2005/2451; A61M 5/2033; A61M 5/2053;
A61M 5/24; A61M 2005/2403; A61M
5/2422; A61M 5/28; A61M 5/281; A61M
5/284; A61M 2205/10; A61M 2205/106;
A61M 2205/12; A61M 2205/123; A61M
2005/3143; A61M 5/31596; A61M
2005/31598; A61M 5/3294; A61M
2205/50; A61M 2205/33
See application file for complete search history.

(56) References Cited

U.S. PATENT DOCUMENTS

| | | |
|---|---|---|
| 2003/0064198 A1 | 4/2003 | Thomsen et al. |
| 2004/0180216 A1 | 9/2004 | Veerasamy et al. |
| 2005/0010168 A1 | 1/2005 | Kendall |
| 2006/0008656 A1 | 1/2006 | Veerasamy |
| 2009/0118669 A1 | 5/2009 | Bendek et al. |
| 2009/0324858 A1 | 12/2009 | Jaeger |
| 2012/0310157 A1 | 12/2012 | Ishikawa et al. |
| 2013/0059087 A1 | 3/2013 | Veerasamy et al. |
| 2013/0059160 A1 | 3/2013 | Veerasamy et al. |
| 2013/0131589 A1 | 5/2013 | Mudd et al. |
| 2013/0273377 A1 | 10/2013 | Veerasamy |
| 2014/0148760 A1* | 5/2014 | Ishikawa .............. A61M 5/20 604/125 |
| 2015/0051538 A1 | 2/2015 | Hata et al. |
| 2015/0174209 A1 | 6/2015 | Chiquette et al. |
| 2015/0218877 A1 | 8/2015 | Kawahara et al. |
| 2016/0361496 A1* | 12/2016 | Guillermo ......... A61M 5/16877 |

FOREIGN PATENT DOCUMENTS

| | | |
|---|---|---|
| CN | 103889483 A | 6/2014 |
| CN | 104780958 A | 7/2015 |
| EP | 1 422 204 A1 | 5/2004 |
| EP | 2 058 020 A2 | 5/2009 |
| EP | 2 923 715 A1 | 9/2015 |
| EP | 3 175 876 A1 | 6/2017 |
| JP | 2008-521494 A | 6/2006 |
| JP | 2007-238378 A | 9/2007 |
| JP | 2009-279438 A | 12/2009 |
| WO | WO 02/27135 A1 | 4/2002 |
| WO | WO 2012/157520 A1 | 11/2012 |
| WO | WO 2015/165718 A1 | 11/2015 |
| WO | WO 2016/027750 A1 | 2/2016 |
| WO | WO 2016/144857 A1 | 9/2016 |
| WO | WO 2017/019837 A1 | 2/2017 |
| WO | WO 2017/114909 A1 | 7/2017 |
| WO | WO 2017/178168 A1 | 10/2017 |

OTHER PUBLICATIONS

Office Action for JP 2019-540492 dated Mar. 23, 2021.
Office Action for CN 201780063062.9 dated Jan. 7, 2021.

* cited by examiner

AUTO INJECTOR WITH AUTOMATED RECONSTITUTION

CROSS REFERENCE TO RELATED APPLICATIONS

This application is a U.S. National Phase Application of PCT International Application Number PCT/EP2017/072483, filed on Sep. 7, 2017, designating the United States of America and published in the English language, which is an International Application of and claims the benefit of priority to Danish Patent Application No. PA201600616, filed on Oct. 11, 2016. The disclosures of the above-referenced applications are hereby expressly incorporated by reference in their entireties.

The present disclosure relates to an auto injector, such as an electronic auto injector, a system comprising an auto injector, and a related method. The auto injector, the system, and the method provides for reconstitution of a medicament.

BACKGROUND

Hypodermic syringes are widely used to deliver fluids to the body. It is known to have hypodermic syringes applicable for manual operation. However, auto injectors have been developed and are widely used to aid the administering of fluid or medicaments to the body.

Hygiene and cross contamination are important issues in the field of medical devices, such as auto injectors. Especially devices which, upon usage, may be subject to body fluids provide risks of transferring diseases between patients and between patients and health care providers. Therefore, to prevent contamination from one patient to another, many devices, instruments, and other items in the health care domain are single use. However, technology has provided technical devices including components of high value, and therefore, from a costs perspective, it may be desirable that such devices are not to be thrown away after a single use. Auto injectors in particular are becoming increasingly more and more advanced, and therefore it may be undesirable if such auto injectors are to be thrown away after a single use.

In providing a device, such as an auto injector, to be used a multiple number of times and/or for multiple patients, there is a risk of cross contamination between patients and between patients and health care providers.

Furthermore, in some cases, an auto injector, is used to inject a medicament which is provided in two-part or two component form. For example, some medicaments may be provided in a powder or a freeze dried form and will need to be dissolved in a liquid before injection. Thus, typically, a medicament provided in a powder, a freeze dried or a lyophilized form will need to be mixed with a liquid to reconstitute the substance into a form that is suitable for injection.

Such medicaments, and other medicaments provided in a two component form may require procedures to prepare the medicament before injection. For example, some medicaments may be poorly soluble in a solute, and therefore needs to be mixed prior to injecting the medicament. Such procedure may also be known as reconstitution.

Under some circumstances, the reconstitution procedure must be performed at a controlled rate and with a specific energy to ensure appropriate reconstitution.

Conventional injectors typically require a manual mixing and/or reconstitution so that a user for example needs to shake the injector device before injection or to combine the two medicament components using screw-type movements of different parts as seen in e.g. U.S. Pat. No. 4,874,381 issued to Vetter.

Moreover, manual reconstitution procedures typically cannot be performed at a controllable rate and even if procedures for manual reconstitution have been followed, there may still be uncertainty regarding whether the substance is sufficiently reconstituted and ready for making an injection.

SUMMARY

It is an object of the present disclosure to provide an auto injector, such as an electronic auto injector, and a related system and method, which overcomes at least some of the disadvantages of the prior art devices.

The present disclosure provides for an auto injector that may be usable for multiple injections, and a cartridge which is simple and therefore may be disposable. As the auto injector may be used multiple times, the auto injector may comprise more advanced features. This effect is achieved, at least in part, by the present disclosure.

The present disclosure provides for an auto injector that is capable of performing multiple steps of an injection procedure. Thus, avoid or limit relying on correct user operation of certain tasks.

Accordingly, an auto injector is provided, such as an auto injector for administering injection of a medicament, the medicament comprising at least a first medicament component and a second medicament component. The auto injector comprises a housing, a receiving part, an operational module, and a processing unit. The auto injector may be an auto injector configured to be hand-held by an operator, such as a hand-held auto injector.

The receiving part is configured for receiving a syringe containing the medicament, and/or for receiving a cartridge comprising the syringe.

The operational module is configured for interacting with the syringe. The operational module comprises a carrier for attaching to the syringe. The syringe operational module comprises a syringe operational part being configured for moving the carrier in a first mixing direction.

The processing unit is connected to the syringe operational part. The processing unit is configured to operate the syringe operational part to move the carrier to mix at least the first medicament component and the second medicament component to obtain a mixed medicament. The movement of the carrier may have a time varying acceleration profile. The time varying acceleration profile may have a first maximum acceleration in the first mixing direction and a second maximum acceleration in a second mixing direction. The first maximum acceleration and/or the second maximum acceleration may be larger than a predetermined acceleration threshold.

Also disclosed is a system comprising an auto injector and a cartridge. The cartridge comprises a syringe and a syringe casing. The auto injector comprises a housing, a receiving part, an operational module, and a processing unit.

The syringe comprises a compartment containing a medicament. The medicament comprises at least a first medicament component and a second medicament component. The syringe has a first syringe end and a second syringe end. The syringe has a syringe opening for fluid communication with the compartment at the first syringe end. The syringe comprises a first stopper. The first stopper is movable inside the compartment at least in a first stopper direction, e.g. along a stopper axis.

The syringe casing comprises a main body configured for receiving the syringe.

The receiving part configured for receiving the cartridge.

The operational module is configured for interacting with the syringe. The operational module comprises a carrier for attaching to the syringe. The operational module comprises a syringe operational part being configured for moving the carrier in a first mixing direction.

The processing unit is connected to the syringe operational part. The processing unit is configured to operate the syringe operational part to move the carrier to mix at least the first medicament component and the second medicament component to obtain a mixed medicament. The movement of the carrier may have a time varying acceleration profile. The time varying acceleration profile may have a first maximum acceleration in the first mixing direction and a second maximum acceleration in a second mixing direction. The first maximum acceleration and/or the second maximum acceleration may be larger than a predetermined acceleration threshold.

Also disclosed is a method for administering injection of a medicament contained in a syringe, e.g. by using an auto injector, and/or a method for preparing a medicament in an auto injector. The medicament comprises at least a first medicament component and a second medicament component. The auto injector comprises an operational module.

The method comprises moving the syringe by operation of the operational module to mix the first medicament component and the second medicament component to obtain a mixed medicament. The movement of the syringe has a time varying acceleration profile. The time varying acceleration profile may have a first maximum acceleration in a first mixing direction and a second maximum acceleration in a second mixing direction. The first maximum acceleration and/or the second maximum acceleration may be larger than a predetermined acceleration threshold.

In some embodiments the predetermined acceleration threshold may be a minimum acceleration threshold. Thus, it may be ensured that at least a minimum acceleration is obtained in the first mixing direction and/or in the second mixing direction. Hereby, a certain degree of mixing may be achieved and/or ensured.

The auto injector and/or the syringe may allow visual inspection of the mixed medicament, e.g. the mixing and/or the mixed medicament may be visually controlled by a user.

The mixing procedure may be optimized to ensure that the certain degree of mixing is achieved. For example, in case the two or more medicaments are completely soluble, the certain degree of mixing may include that the first and/or second medicament, etc. is at least 70%, such as at least 80%, such as at least 90%, such as at least 95%, dissolved in the second and/or first medicament, etc.

For example, in the case of providing a suspension, the mixing procedure may be optimized to ensure that the certain degree of mixing is achieved, for example, in that a syringable suspension is provided, in that for example a mean particle size of particles in the mixed medicament is below a threshold, such as below 100 µm, such as between 0.5 µm-100 µm, such as between 0.5 µm-50 µm, such as between 1-10 µm, such as above 0.5 µm. "mean particle size" refers to volume mean diameter as may be measured by laser-light scattering methods (LLS). Particle size may be measured by LLS methods and mean particle size may be calculated from the particle size distribution. The certain degree of mixing may ensure that at least 70%, such as at least 80%, such as at least 90% of the theoretically possible dose may be injected.

It is an advantage of the present disclosure that a procedure for preparing a medicament, such as mixing or reconstitution of a medicament may be performed automatically by an auto injector, thereby, the need for a manual operation may be limited, and, thus, the risk of human errors in preparing the medicament and/or injection may be reduced.

Furthermore, the present disclosure may provide that the mixing may be preformed without preoccupying the person preparing the medicament. This may especially be an advantage if mixing of the medicament is time consuming, e.g. takes more than 5 seconds, such as more than 10 seconds, such as more than 20 seconds, such as more than 60 seconds, such as more than 2 minutes, such as several minutes.

A cartridge, such as the cartridge of the disclosed system, and/or a cartridge for use in the disclosed auto injector, comprises a syringe.

The syringe comprises a compartment configured to contain the medicament. The medicament comprises at least a first medicament component and a second medicament component. The syringe has a first syringe end and a second syringe end. The syringe has a syringe opening for fluid communication with the compartment at the first syringe end. The syringe comprises a first stopper movable inside the compartment at least in the first stopper direction along a stopper axis.

The cartridge may comprise a syringe casing. The syringe casing may comprise a main body. The main body may be configured for receiving the syringe, and/or the main body may be attached to the syringe. The main body may have a tube part and/or a front end. The tube part may extend along a tube axis. The tube axis may be parallel or coinciding with the stopper axis.

The syringe may be movable relative to the main body of the syringe casing, e.g. when the syringe is received in the main body. For example, the syringe may be movable along the tube axis and/or the stopper axis, e.g. from a first position to a second position relative to the front end of the main body.

The syringe casing may comprise an inner body attachable to the syringe. The main body and/or the tube part may enclose the inner body. The inner body may be movable relative to the main body. For example, the inner body may be movable relative to the main body along the tube axis and/or the stopper axis. The inner body may provide a guided movement of the syringe relative to the main body.

The syringe comprises a compartment configured for containing the medicament. The syringe has a first syringe end and a second syringe end. The syringe has a syringe opening for fluid communication with the compartment at the first syringe end. A stopper, such as the first stopper, may limit the compartment in the second end whereas the compartment in the first end may be limited by the syringe opening. Thus, the compartment may be confined by compartment walls of the syringe, the stopper, such as the first stopper, and the syringe opening.

The compartment of the syringe may contain the medicament. The medicament may be a fluid and/or a liquid. The medicament may be an aqueous solution, e.g. saline. The medicament may comprise a plurality of medicament components and comprises at least a first medicament component and a second medicament component. The compartment of the syringe may contain the plurality of medicament components, and may thus comprise at least the first medicament component and the second medicament component.

Each of the plurality of medicament components may be a powder composition, a fluid, a liquid, a gel, and/or any combination thereof. The first medicament component and/ or the second medicament component may be a powder composition. The first medicament component and/or the second medicament component may be a fluid composition, such as a liquid composition. The first medicament component may be a powder composition and the second medicament component may be a fluid composition, e.g. water or ethanol. The first medicament component may be a solute. The second medicament component may be a solvent. It is envisaged that the medicament may be any medicament being injectable via a syringe, for example after reconstitution of the medicament.

The syringe may be a multi chamber syringe, e.g. the compartment of the syringe may comprise a plurality of compartment parts. For example, the syringe may be a dual chamber syringe, e.g. the compartment of the syringe may comprise a first compartment part and a second compartment part.

Compartment parts may be divided by a stopper, such as a second stopper and/or a third stopper. For example, the syringe may comprise a second stopper between the first syringe end and the first stopper. The second stopper may divide the compartment into a first compartment part and a second compartment part. The second stopper may be movable inside the compartment, e.g. at least in the first stopper direction, such as along the stopper axis. The stopper axis may be parallel or coinciding with the tube axis.

A bypass section, such as a middle bypass section, may be provided in the syringe between neighbouring compartment parts. The compartment may comprise one or more bypass sections, such as the middle bypass section and/or a front bypass section, etc. Bypass sections may provide fluid communication between compartment parts when a stopper is positioned in the bypass section. For example, when the second stopper is positioned in the middle bypass section, the first compartment part may be in fluid communication with the second compartment part.

Each compartment part may be configured to contain a component of the medicament, and/or each of the plurality of compartment parts may comprise a medicament component. The first compartment part may contain the first medicament component. The first medicament component may be provided in the first compartment part. The second compartment part may contain the second medicament component. The second medicament component may be provided in the second compartment part.

In some embodiments, all medicament components, such as for example, the plurality of medicament components, such as at least the first medicament component and the second medicament component may not need to be physically separated. Thus, providing a plurality of medicament components does not necessarily require the compartment to be divided into a plurality of compartment parts.

The present device is generally useful for administration of a drug which is injected as a suspension.

The medicament may be a suspension, e.g. a liquid, such as water or an aqueous solution, comprising solid particles of one or more compound(s). The solid particles may be evenly distributed in the liquid. When a medicament is administered as a suspension, the solid particles typically comprise the active ingredient of the medicament, or the main part of the active ingredient. The risk of tissue damage on injection or injection site pain depends on factors such as choice of active ingredient and particle size. The mean particle size or the active ingredient (or other non-dissolved components) can be below 100 μm, such as 0.5 μm-100 μm, such as 0.5 μm-50 μm, such as 1 μm-10 μm. "mean particle size" refers to volume mean diameter as may be measured by laser-light scattering methods (LLS). Particle size may be measured by LLS methods and mean particle size may be calculated from the particle size distribution. Suspensions can be prepared from a poorly soluble compound and/or compounds, e.g. a compound with a solubility below 0.1 mg/ml in the liquid.

The medicament or an active ingredient of the medicament may comprise a poorly soluble medicament component, such as a medicament component having solubility in the solvent of less than 0.1 mg/ml. The medicament may be a powder composition, a lyophilised medicament, etc.

A reusable auto injector, such as the disclosed auto injector, may be especially useful when the syringe comprises more than one compartment or more than one chamber. For example an auto injector for a multi compartment or multi chamber syringe may be more advanced, and therefore it may be beneficial to allow the auto injector to be used more than one time. For example, the auto injector may provide automated processes for mixing medicament components, such as for mixing medicament components initially provided in different compartments of the syringe.

In one or more embodiments, a reusable auto injector, such as the disclosed auto injector may be particular useful when the medicament comprises more than one medicament component so that mixing of the medicament components may be performed by a reusable auto injector configured to provide automated processes for mixing medicament components, such as for mixing medicament components initially provided in a same compartment of the syringe, but for which reconstitution is preferred before injection.

The auto injector may be configured for specific medication and/or specific patients. The auto injector may provide increased possibility for injecting the medicament in certain patients, such as in schizophrenic patients.

Movement of the syringe and/or the carrier, such as a carrier for attaching to the syringe, may follow a path, such as a programmed path, such as a sequence of movements in one or more directions. For example, the syringe and/or the carrier may be moved in the first mixing direction followed by a movement the second mixing direction. The second mixing direction may be opposite the first mixing direction.

The syringe operational part may be configured for moving the carrier and/or the syringe in the first mixing direction. The syringe operational part may be configured for moving the carrier and/or the syringe in the second mixing direction.

The syringe operational part may be configured to move the syringe and/or the carrier, and the syringe operational part may thus be configured to move the syringe and/or the carrier along a path, such as along a programmed path, such as in a sequence of movements in one or more directions, etc. The auto injector may comprise a processing unit and the processing unit may be programmed to control the syringe operational part to move the syringe and/or the carrier in predetermined patterns of movement, such as in movements having maximum acceleration in one or more directions, such as maximum accelerations above one or more predetermined threshold acceleration, in movements having time varying velocity profiles, time varying acceleration profiles, etc.

In some embodiments, the movement of the syringe and/or the carrier may have a time varying velocity profile and/or a time varying acceleration profile. The time varying velocity profile may designate actual velocity of the syringe and/or the carrier between a start time and a stop time. The time varying acceleration profile may designate actual acceleration of the syringe and/or the carrier between a start time and a stop time.

The time varying velocity profile and/or the time varying acceleration profile may vary over time, such as vary periodically over time.

The time varying acceleration profile and/or the time varying velocity profile may have one or more maxima. For example, the time varying acceleration profile may have a first maximum acceleration in the first mixing direction and/or a second maximum acceleration in the second mixing direction. Alternatively or additionally, the time varying velocity profile may have a first maximum velocity in the first mixing direction and/or a second maximum velocity in the second mixing direction.

The maxima may be denoted by their magnitude. For example, one or more acceleration maxima, such as the first acceleration maximum and/or the second acceleration maximum, may be the magnitude of the respective acceleration maximum. Alternatively or additionally, one or more velocity maxima, such as the first velocity maximum and/or the second velocity maximum, may be the magnitude of the respective velocity maximum.

One or more of the maxima may be larger than a predetermined threshold. The first maximum acceleration and/or the second maximum acceleration may be larger than a predetermined acceleration threshold. The first maximum velocity and/or the second maximum velocity may be larger than a predetermined velocity threshold. The predetermined acceleration threshold may be 1 m/s$^2$, such as 2 m/s$^2$, such as 3 m/s$^2$. The predetermined velocity threshold may be 50 mm/s, such as 70 mm/s, such as 100 mm/s The time varying acceleration profile may be varying over time, e.g. between −2 m/s$^2$ and 2 m/s$^2$. The time varying acceleration profile having time varying acceleration, such as acceleration in the first mixing direction and acceleration in the second mixing direction, may facilitate mixing of the medicament.

The time varying velocity profile may be varying over time, e.g. between −100 mm/s and 100 mm/s. The time varying velocity profile having time varying velocity, such as movement in the first mixing direction and movement in the second mixing direction, may facilitate mixing of the medicament.

The time varying velocity profile and/or the time varying acceleration profile may have periods of constant velocity and/or acceleration, respectively. Constant velocity and/or acceleration may be velocity and/or acceleration, respectively, which is maintained for at least 0.1 seconds, such as more than 0.1 seconds, such as more than 0.2 seconds.

The time varying velocity profile may have a first constant velocity in the first mixing direction. The first constant velocity may be the first maximum velocity. The time varying velocity profile may have a second constant velocity in the second mixing direction. The second constant velocity may be the second maximum velocity.

The time varying velocity profile and/or the time varying acceleration profile may resemble a certain wave. The time varying velocity profile and/or the time varying acceleration profile may resemble a sine wave. The time varying velocity profile and/or the time varying acceleration profile may resemble a trapezoid wave. The time varying velocity profile and/or the time varying acceleration profile may resemble a sawtooth wave. The time varying velocity profile and/or the time varying acceleration profile may resemble a rectangular wave. The time varying velocity profile and/or the time varying acceleration profile may resemble a triangular wave.

The time varying velocity profile may have an amplitude and/or a frequency. For example, the amplitude may be between 100-250 mm/s, such as 170 mm/s. The frequency may be between 1-5 Hz, such as 3 Hz.

The mixing procedure may be performed over a period a time, e.g. from a start time to a stop time. Moving the carrier and/or the syringe may be continued for a predetermined duration of time. Moving the carrier and/or the syringe may comprise moving the carrier and/or the syringe for a predetermined duration. For example, operating the syringe operational part may comprise moving the carrier for a predetermined duration of time, such as alternatingly moving the carrier in the first mixing direction and the second mixing direction for the predetermined duration of time. The predetermined duration of time may be more than 5 seconds, such as more than 10 seconds, such as more than 20 seconds, such as more than 60 seconds, such as more than 2 minutes, such as several minutes.

In one or more embodiments, the movement and/or the mixing procedure is performed in accordance with properties, such as solubility properties of the at least first and second medicament components. Typically, the movements, the movement pattern and/or the mixing procedure is configured to ensure proper mixing of the at least first and second medicament components, so as to ensure a mean particle size below a threshold, such as below 100 μm, such as 0.5 μm-100 μm, such as 0.5 μm-50 μm, such as 1 μm-10 μm. The auto injector and/or the syringe may allow visual inspection of the mixed medicament, e.g. the mixing and/or the mixed medicament may be visually controlled by a user.

The first stopper of the syringe may be moved, e.g. the method may comprise moving the first stopper. Movement of the first stopper may be achieved by operation of the operational module. For example, the first stopper may be moved in the first stopper direction, e.g. by operation of the operational module, to expel the mixed medicament through the syringe opening of the syringe. Alternatively or additionally, the first stopper may be moved in the first stopper direction, e.g. by operation of the operational module, to combine the first medicament component and the second medicament component. In some embodiments the mere combination of the first medicament component and the second medicament component may not ensure proper mixing of the first and second medicament components.

The operational module may comprise a stopper operational part. The processing unit may be connected to the stopper operational part. The stopper operational part may be configured for moving a stopper, such as a first stopper of the syringe, e.g at least in a first stopper direction and/or in a second stopper direction. The first stopper direction and/or the second stopper direction may be along the stopper axis. The stopper operational part may be configured for moving the first stopper by movement of a plunger rod in the first stopper direction and/or in the second stopper direction. The stopper operational part may be configured for moving the first stopper at least in the first stopper direction, e.g. to expel medicament through the syringe opening, and/or to advance the medicament towards the first end of the syringe. Furthermore, the stopper operational part may be configured for moving a stopper, such as a second stopper, to a bypass section for allowing combination of more medicament components positioned in more compartment parts, such as combination of the first medicament component and the second medicament component.

A plunger rod is throughout the present disclosure to be understood as any means capable of moving a stopper of a syringe in a first and/or second direction. The plunger rod may form part of an auto injector.

The first medicament component and the second medicament component may be separated. For example, the first medicament component and the second medicament component may be separated by a stopper, such as a second stopper of the syringe. The processing unit may be configured to operate the stopper operational part to move the first stopper of the syringe a first stopper distance in the first stopper direction to combine the first medicament component and the second medicament component. For example, the first medicament component and the second medicament component may be combined prior to mixing the first medicament component and the second medicament component.

The processing unit may be configured to operate the stopper operational part to move the first stopper in the first stopper direction to expel the mixed medicament through the syringe opening. For example the mixed medicament may be expelled after mixing the first medicament component and the second medicament component. The medicament, such as the mixed medicament, may be expelled during injection of the medicament, such as the mixed medicament.

The first mixing direction and the first stopper direction may be parallel. The first mixing direction may be along the stopper axis. The second mixing direction may be along the stopper axis.

A needle may be attached to the syringe, and/or the syringe may comprise a needle. The method may comprise moving the syringe, e.g. in the first mixing direction, e.g. by operation of the operational module, to advance a needle of the syringe. The processing unit may be configured to operate the syringe operational part to advance the needle, such as a needle attached to the syringe. For example, the needle may be advanced to insert the needle into tissue of a patient. The needle may be advanced after mixing the first medicament component and the second medicament component, and/or prior to expelling the medicament.

The operational module and/or the auto injector and/or the receiving part may comprise a syringe lock. The syringe lock may have a locked state and an unlocked state. The syringe lock may be configured to lock the syringe to the carrier in the locked state. Thus, the syringe lock may lock the syringe to the carrier when the syringe is received in the receiving part of the auto injector and thus lock the syringe to the auto injector, such as lock the syringe to the auto injector during use of the auto injector. The syringe lock may be unlocked upon completion of the injection. Thus, after injection of the medicament, the syringe lock may be unlocked to allow the syringe to be removed from the receiving part, i.e. from the auto injector, to allow the used syringe to be discarded.

The plunger rod may be configured to bring the syringe lock to the unlocked state by a predefined movement in the second stopper direction. For example, a retraction and/or a full retraction of the plunger rod may cause the syringe lock to be in the unlocked state. Alternatively or additionally, the plunger rod may be configured to bring the syringe lock to the locked state by a predefined movement in the first stopper direction.

The syringe lock may comprise a first syringe locking member. The first syringe locking member may be in a first position when the syringe lock is in the locked state. The first syringe locking member may be in a second position when the syringe lock is in the unlocked state. The first syringe locking member may be biased towards the first position. The first syringe locking member may be configured to be forced to the second position by a predefined movement of a plunger rod, such as a plunger rod of the auto injector and/or of the operational module. The plunger rod, such as the plunger rod of the auto injector and/or of the operational module, may be configured to force the first syringe locking member to the second position by a predefined movement in the second stopper direction. For example, a retraction and/or a full retraction of the plunger rod may force the first syringe locking member to the second position.

The syringe lock may comprise a second syringe locking member. The second syringe locking member may be in a first position when the syringe lock is in the locked state. The second syringe locking member may be in a second position when the syringe lock is in the unlocked state. The second syringe locking member may be biased towards the first position. The second syringe locking member may be configured to be forced to the second position by a predefined movement of a plunger rod, such as the plunger rod of the auto injector and/or of the operational module. The plunger rod, such as the plunger rod of the auto injector and/or of the operational module may be configured to force the second syringe locking member to the second position by a predefined movement in the second stopper direction. For example, a retraction and/or a full retraction of the plunger rod may force the second syringe locking member to the second position.

The syringe lock may comprise a plurality of syringe locking members. The plurality of syringe locking members may include the first syringe locking member and the second syringe locking member.

The operational module may comprise a driver and/or a plurality of drivers, such as a stopper driver and/or a syringe driver. The driver(s) may be configured to drive one or more operational part(s) of the operational module. For example, the stopper driver may be configured to drive the stopper operational part and/or the syringe driver may be configured to drive the syringe operational part.

The driver(s), such as the stopper driver and/or the syringe driver, may be a motor, such as an electro-mechanical motor, such as a DC motor, e.g. a DC motors with or without brushes. For example, the stopper driver may be a brushed DC motor and/or the syringe driver may be a brushless DC motor. A brushless DC motor may be preferred due to higher durability of a brushless DC motor. Especially for the syringe driver, a brushless DC motor may be preferred due to many and/or rapid movements performed by the syringe driver. Brushed DC motors are generally cheaper than brushless DC motors. Therefore brushed DC motors may be preferred from a cost perspective. A brushed DC motor may be preferred for the stopper driver.

The auto injector may comprise a processing unit. The processing unit may be connected to the operational module. The processing unit may be configured to operate the operational module, such as the syringe operational part and/or the stopper operational part and/or the stopper driver and/or the syringe driver.

A user of the devices of the present disclosure may be a health care provider and/or a patient. There may be a plurality of users of the devices of the present disclosure, such as a first user and/or a second user and/or a third user. A patient may be a user of the device, e.g. the first user and/or the third user. A health care provider may be a user of the device, e.g. the second user.

In some embodiments the syringe may be manufactured with an attached needle. For example, the needle may be fixedly attached to the syringe. In other embodiments, the syringe and the needle may be manufactured separately, and the user, e.g. a health care provider, may attach the needle before use.

It is envisaged that any embodiments or elements as described in connection with any one aspect may be used with any other aspects or embodiments, mutatis mutandis. For example, the plunger lock disclosed in relation to the system, cartridge, and/or auto injector may be the plunger lock as also disclosed. The cartridge disclosed in relation to the system may be the cartridge as also disclosed. The auto injector disclosed in relation to the system may be the auto injector as also disclosed.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

DETAILED DESCRIPTION

Figure 1:
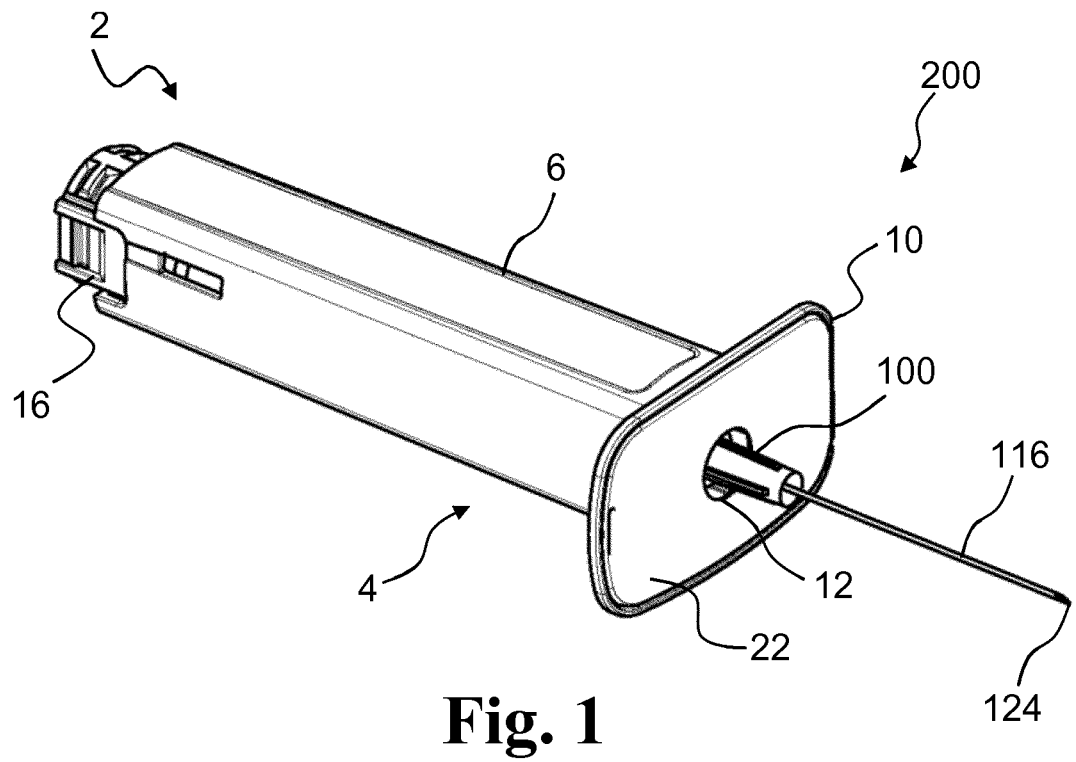
FIG. 1 schematically illustrates an exemplary cartridge for an auto injector.

Various embodiments are described hereinafter with reference to the figures. Throughout, the same reference numerals are used for identical or corresponding parts. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 schematically illustrates an exemplary cartridge 200 for an auto injector. The cartridge 200 comprises a syringe casing 2 and a syringe 100. The syringe 100 may contain a medicament.

In the example depicted, the syringe comprises a needle 116 with a needle tip 124. The needle 116 may be a hypodermic needle, and the needle tip 124 may be adapted for penetrating skin and insertion into body tissue, such as muscle tissue and/or adipose tissue. The syringe 100 may be fitted with the needle 116, or the needle 116 may be removably attached to the syringe 100.

The syringe casing 2 comprises a main body 4. The main body 4 has a tube part 6 and a front end 10. The tube part 6 extends along a tube axis, e.g. a longitudinal axis of the tube part 6 and/or of the syringe casing 2. The tube part 6 is configured for receiving and/or enclose the syringe 100.

The front end 10 has a front end opening 12. The front end opening 12 of the front end 10 allows for passage of the needle 116. The front end 10 further has a front surface 22 configured to abut a user's skin before injection of the medicament.

The syringe casing 2 comprises an optional inner body 16. The inner body 16 is attached to the syringe 100. The tube part 6 encloses the inner body 16, or at least a part of the inner body 16. The inner body 16 is movable relative to the main body 4. In the example depicted, the inner body 16 is movable relative to the main body 4 along the tube axis. In alternative exemplary syringe casings the inner body 16 may be omitted and the tube part 6 may be attachable to the syringe.

The tube part 6 and the front end 10 may provide for needle protection after use. The syringe 100 may be retracted relative to the tube part 6, such that the needle 116 is enclosed in the tube part 6. The front end opening 12 may have a size which prevents contact with the needle tip 124, e.g. according to relevant industry standards, such as the ISO 23908-2011, when the syringe 100 is in a fully retracted position, such as in a locked position. For example, the covered main body inscribed opening diameter may be smaller than 2 times the distance to a needle tip of a needle attached to the syringe, when the syringe is in a retracted position, such as in the locked position.

Figure 2:
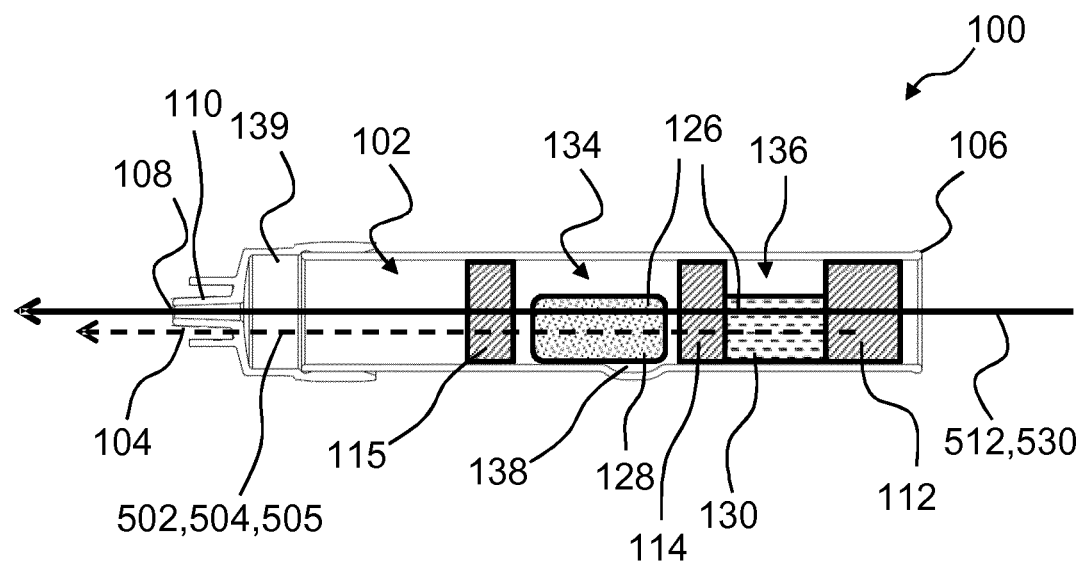
FIG. 2 schematically illustrates an exemplary syringe.

FIG. 2 schematically illustrates an exemplary syringe 100. The syringe 100 may be attached to a syringe casing 2 as described in relation to other figures. The syringe 100 comprises a compartment 102 configured for containing a medicament 126. In the depicted example, the syringe 100 is a dual chamber syringe and the medicament 126 is comprised by a first medicament component 128, e.g. a powder or cake composition, and a second medicament component 130, e.g. a fluid or a liquid component. In other embodiments, the medicament 126 may be a single component and/or the syringe 100 may be a single chamber syringe or the syringe 100 may have a plurality of chambers higher than two.

The syringe 100 has a first syringe end 104 and a second syringe end 106. The syringe 100 extends along a syringe axis 530 between the first syringe end 104 and the second syringe end 106. The syringe has a syringe opening 108 at the first syringe end 104. The syringe opening 108 provides fluid communication with the compartment 102. The syringe 100 is configured to expel the medicament 126 through the syringe opening 108. The syringe 100 comprises an optional first syringe channel 110, and the syringe 100 is configured to expel the medicament 126 through the first syringe channel 110. The syringe opening 108 is a syringe opening of the first syringe channel 110.

The syringe 100 comprises a first stopper 112 movable inside the compartment 102.

The first stopper 112 is movable at least in a first stopper direction 502 from the second syringe end 106 towards the first syringe end 104. The first stopper 112 may be movable in a second stopper direction 503. The second stopper direction 503 may be opposite the first stopper direction 502.

The syringe 100, as depicted, furthermore comprises an optional second stopper 114 between the first syringe end 104 and the first stopper 112. The second stopper 114 is movable inside the compartment 102. The second stopper 114 is movable at least in a first stopper direction 504 for the second stopper 114. As depicted, the first stopper direction 504 for the second stopper 114 may be the same direction as the first stopper direction 502. The second stopper divides the compartment 102 into a first compartment part 134 and a second compartment part 136. The first compartment part 134 contains the first medicament component 128. The second compartment part 136 contains the second medicament component 130. The compartment 102 furthermore comprises a middle bypass section 138. The middle bypass section 138 provides the possibility for fluid communication between the first compartment part 134 and the second compartment part 136, thereby providing that the first medicament component 128 may be combined with the second medicament component 130. When the second stopper 114 is positioned in the middle bypass section 138, the first compartment part 134 is in fluid communication with the second compartment part 136. In embodiments wherein the second stopper 114 is omitted, the middle bypass section 138 may also be omitted.

The syringe 100, as depicted, furthermore comprises an optional third stopper 115 between the first syringe end 104 and the second stopper 114. The third stopper 115 is movable inside the compartment 102. The third stopper 115 is movable at least in a first stopper direction 505 for the third stopper 115. As depicted, the first stopper direction 505 for the third stopper 115 may be the same direction as the first stopper direction 502 for the first stopper 112 and/or the first stopper direction 504 for the second stopper 114. The third stopper 115 provides a seal between a compartment part containing the medicament 126, such as the first compartment part 134 and/or the second compartment part 136, from the syringe opening 108. The compartment 102 furthermore comprises a front bypass section 139. The front bypass section 139 provides the possibility for fluid communication between the compartment part containing the medicament 126, such as the first compartment part 134 and/or the second compartment part 136, and the syringe opening 108. When the third stopper 115 is positioned in the front bypass section 139 the compartment part containing the medicament 126, such as the first compartment part 134 and/or the second compartment part 136, is in fluid communication with syringe opening 108 to allow the medicament 126 to be expelled through the syringe opening 108. In embodiments wherein the third stopper 115 is omitted, the front bypass section 139 may also be omitted.

The first stopper 112, the second stopper 114, and/or the third stopper 115 may be movable along a stopper axis 512. The first stopper direction 502 for the first stopper 112, the first stopper direction 504 for the second stopper 114, and/or the first stopper direction 505 for the third stopper 115 may be along the stopper axis 512. The stopper axis 512 may, as illustrated, be parallel and/or coinciding with the syringe axis 530.

Figure 3:
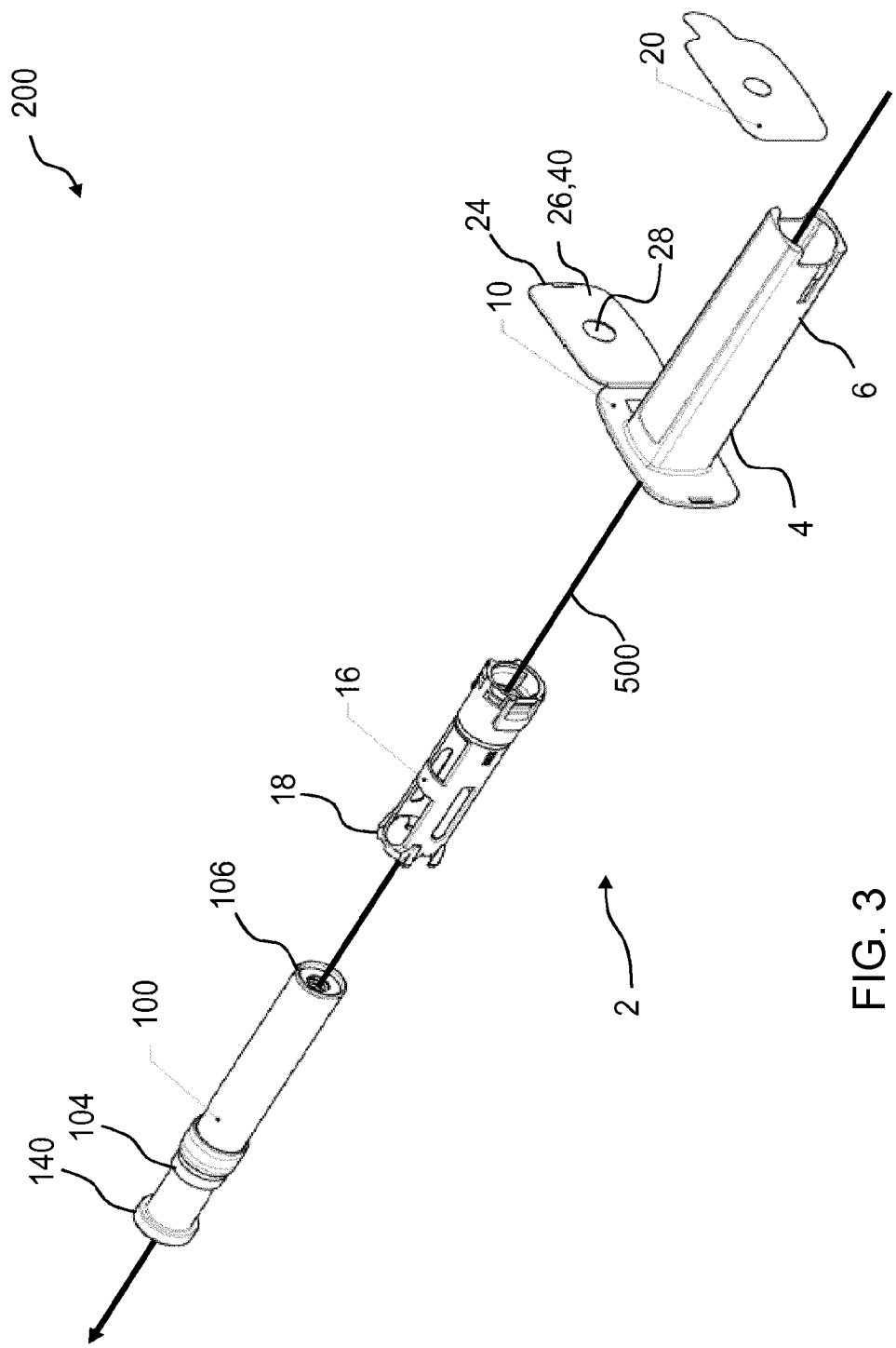
FIG. 3 shows an exploded view of an exemplary cartridge for an auto injector.

FIG. 3 shows an exploded view of an exemplary cartridge 200 for an auto injector. The cartridge 200 comprises a syringe casing 2 and a syringe 100.

The syringe casing 2 comprises a main body 4 and an inner body 16. The main body 4 has a tube part 6 and a front end 10.

The syringe casing 2 comprises an optional cover element 24. The cover element 24 has a cover part 26 and a cover opening 28. The cover element 24 is movable relative to the front end 10 between a first position and a second position. In the example depicted, the cover element 24 is in the first position. In the second position (not shown), the cover part 26 covers at least a portion of the front end opening, and the cover opening 28 and the front end opening 12 forms a covered main body opening for allowing passage of a needle, e.g. a needle attached to the syringe 100. A removable sheet 20 may be configured to cover at least a part of a cover surface 40 of the cover element 24, and/or the removable sheet 20 may be configured to completely cover the cover surface 40 of the cover element 24. When the cover part 26 is in the second position, the cover surface 40 may form the front surface 22 of the front end 10 as described in relation to other figures.

The syringe casing 2 comprises an optional locking element 18. In the depicted example, the inner body 16 comprises the locking element 18. The locking element 18 is configured for preventing the inner body 16 from moving towards the front end 10, when the inner body 16 is in a locked position, e.g. in a fully retracted position.

The syringe 100 comprises a first syringe end 104 and a second syringe end 106. The syringe 100 may comprise an optional syringe cap 140 at the first syringe end 104. The syringe cap 140 may be removable, and provided for protection of the medicament contained in the syringe. For example, the syringe cap 140 may be configured for covering a syringe opening of the syringe 100. The cover element 24 of the syringe casing 2 provides needle protection in situations where the syringe 100 is fitted with a syringe cap 140, and therefore is not able to fit through an opening which fulfils the requirements for needle protection. Furthermore, the cover element 24 enables the syringe 100 to be front loaded into the syringe casing 2, where after the cover element 24 may be used to reduce the size of the opening to fulfil requirements for needle protection.

As depicted, both syringe 100 and the syringe casing 2, such as the main body 4, the tube part 6, and/or the inner body 16, may extend along the same longitudinal axis, e.g. the tube axis 500.

Figure 4:
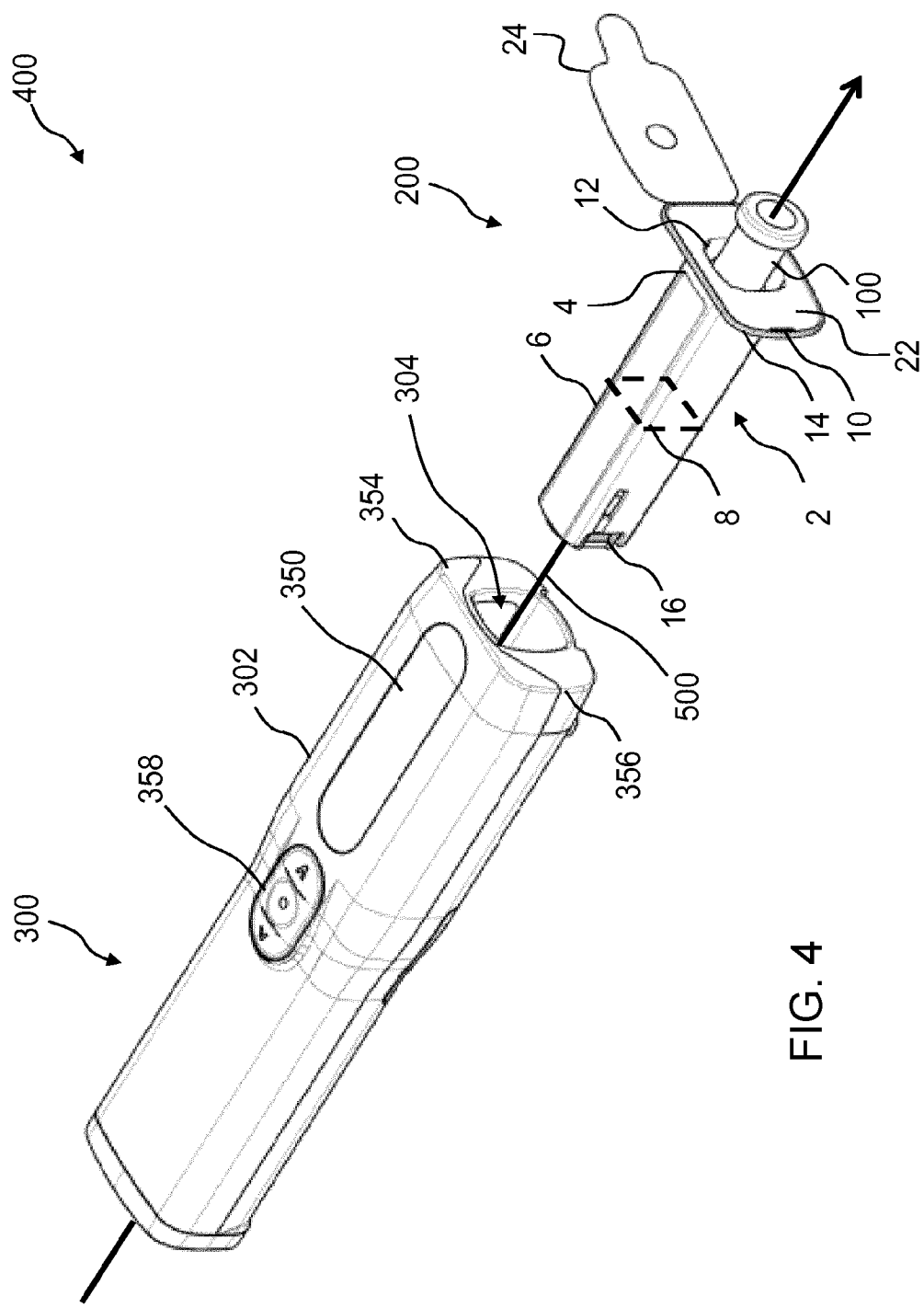
FIG. 4 schematically illustrates an exemplary system.

FIG. 4 schematically illustrates an exemplary system 400 comprising an auto injector 300 and a cartridge 200 comprising a syringe 100 containing a medicament and/or configured for containing a medicament. The cartridge 200 is configured to be received in the auto injector 300, and the auto injector 300 is configured for administering injection of the medicament contained in the syringe 100 of the cartridge 200. The auto injector 300 may be used multiple times. The cartridge 200 may be discarded after use, e.g. after each use, and a new cartridge 200 may be inserted into the auto injector for a subsequent use.

The auto injector 300 comprises a housing 302 and a receiving part 304 configured for receiving the cartridge 200. The auto injector 300 furthermore comprises an operational module (not visible) configured for interacting with the cartridge 200. The operational module may be enclosed in the housing 302.

The cartridge 200 comprises the syringe 100 and a syringe casing 2, which have been further described in relation to other figures.

The tube part 6 extends along the tube axis 500, and the tube part has a tube part outer perimeter 8 in a first tube plane perpendicular to the tube axis. The front end 10 has a front end outer perimeter 14 in a second tube plane perpendicular to the tube axis. The auto injector comprises a housing front part 354. The housing front part 354 has a housing front part outer perimeter 356 in a third tube plane perpendicular to the tube axis 500, such as when the cartridge 200 is received in the receiving part 304 of the auto injector 300.

The front end outer perimeter 14 circumscribes an area larger than, or equal to, an area circumscribed by the housing front part outer parameter 356. The front end 10 covers, and/or completely covers, the housing front part 354 when the cartridge 200 is received in the receiving part 304. This decreases the risk of contaminating the auto injector 300, which is especially important if the auto injector 300 is to be used by multiple users, e.g. multiple patients.

The front end outer perimeter 14 circumscribes an area larger than an area circumscribed by the tube part outer parameter 8. Thereby, the cartridge 200 may for example be suitable for front loading into the auto injector 300 as the front end 10 may provide a stop for inserting the cartridge into the receiving part 304 of the auto injector 300.

The auto injector 300 comprises an optional display unit 350 for visually displaying information to a user of the auto injector, e.g. to a health care provider. The auto injector 300 comprises an optional user interface 358 for receiving a user input from a user of the auto injector, e.g. a health care provider. The user interface 358 may, as also illustrated, comprise one or more push buttons.

Figure 5:
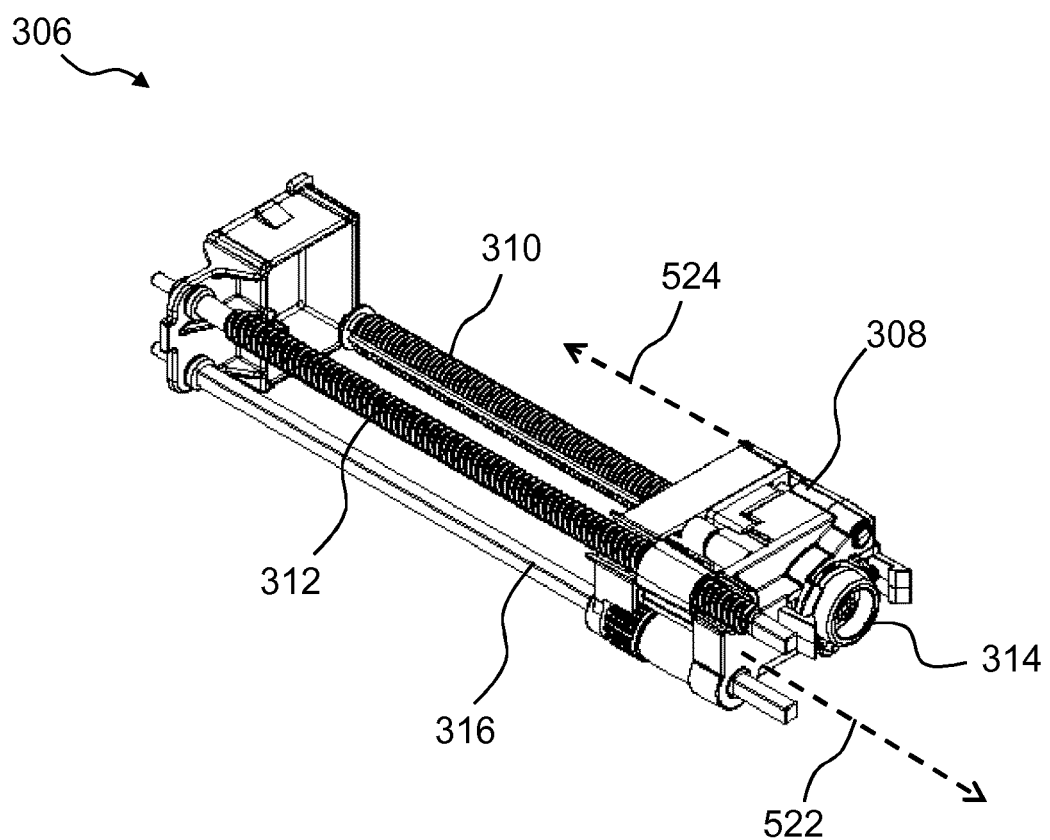
FIG. 5 schematically illustrates an exemplary operational module.

FIG. 5 schematically illustrates an exemplary operational module 306 for an auto injector, such as the auto injector 300 as described in relation to other figures. The operational module 306 is configured for interacting with a cartridge, such as the cartridge 200 as described in relation to other figures. The operational module 306 comprises a carrier 308 for attaching to a syringe, such as the syringe 100 as described in relation to other figures. The carrier 308 may be attached to the syringe via attachment to one or more parts of a syringe casing being attached to the syringe. For example, the carrier 308 may be releasably locked to the syringe by a syringe lock.

The operational module 306 comprises a stopper operational part 310. The stopper operational part 310 is configured for moving a stopper of the syringe, such as a first stopper of the syringe. In the depicted example, the stopper operational part 310 is configured for moving the stopper of the syringe by movement of a plunger rod 314 which interacts with the stopper of the syringe. The operational module 306 comprises an optional drive axle 316 which is connected to the stopper operational part 310. The drive axle 316 provides that a driver, such as a DC motor, may control the stopper operational part 310 by operating the drive axle 316. Furthermore, the drive axle 316 provides for control of the stopper operational part 310 independently of a location of the carrier 308.

The operational module 306 comprises a syringe operational part 312. The syringe operational part 312 is configured for moving the syringe. The syringe operational part 312 is configured for moving the syringe by moving the carrier 308 in a first syringe direction 522 and/or in a second syringe direction 524. The carrier 308 may be moved in order to mix a plurality of medicament components, such as a first medicament component and a second medicament component. Thus, the first syringe direction 522 may be a first mixing direction, and/or the second syringe direction 524 may be a second mixing direction. The syringe operational part 312 may further be configured for moving the syringe and/or the carrier 308 in the first syringe direction 522 to advance a needle of the syringe and/or a needle attached to the syringe, e.g. the syringe may be moved in the first syringe direction 522 for penetration of the skin and insertion of the needle into body tissue.

The syringe operational part 312 and the stopper operational part 310 may provide movements which are parallel, e.g. the stopper operational part 310 may provide movement of the plunger rod 314 in a direction parallel to the first syringe direction 522 and/or the second syringe direction 524. The first syringe direction 522 and/or the second syringe direction 524 may be along an axis, such as the tube axis of the syringe casing as described in relation to other figures.

Figure 6:
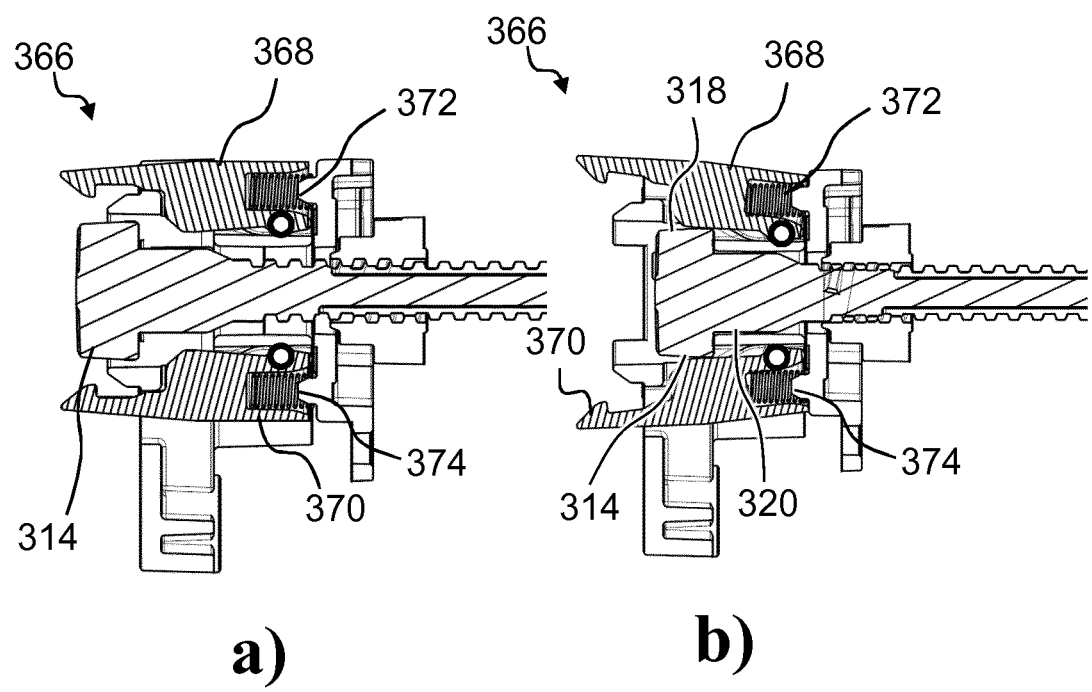
FIG. 6 a-b schematically illustrate an exemplary syringe lock.

FIG. 6a-b schematically illustrates an exemplary syringe lock 366. The auto injector and/or the operational module of the auto injector, as described in relation to other figures, may comprise the syringe lock 366. The syringe lock 366 has a locked state, as shown in FIG. 6a, and an unlocked state, as shown in FIG. 6b. The syringe lock 366 is configured to lock a syringe to the operational module, such as to a carrier of the operational module. For example, the syringe lock 366 may be configured to lock the syringe to the carrier in the locked state.

The syringe lock 366 comprises a first syringe locking member 368. The first syringe locking member 368 is in a first position when the syringe lock 366 is in the locked state, as shown in FIG. 6a. The first syringe locking member 368 is in a second position when the syringe lock 366 is in the unlocked state, as shown in FIG. 6b. The first syringe locking member 368 is biased towards the first position by a first syringe locking member spring 372. The first syringe locking member 368 is configured to be forced towards the second position by a plunger rod 314, such as a plunger rod of the auto injector.

The syringe lock 366 comprises a second syringe locking member 370. The second syringe locking member 370 is in a first position when the syringe lock 366 is in the locked state, as shown in FIG. 6a. The second syringe locking member 370 is in a second position when the syringe lock 366 is in the unlocked state, as shown in FIG. 6b. The second syringe locking member 370 is biased towards the first position by a second syringe locking member spring 374. The second syringe locking member 370 is configured to be forced towards the second position by the plunger rod 314.

The syringe lock 366 may in other embodiments comprise a plurality of locking members, such as a third and/or a fourth and/or a fifth syringe locking member. One or more of the plurality of locking members may be locking members such as the first locking member 368 and/or the second locking member 370.

The plunger rod 314 is configured to force the first syringe locking member 368 and the second syringe locking member 370 to the second position by a predefined movement, such as a predefined movement in a second stopper direction. For example, as illustrated, the plunger rod 314 is configured to force the first syringe locking member 368 and the second syringe locking member 370 to the second position by retracting the plunger rod 314.

The plunger rod 314 has a first plunger rod part 318 and a second plunger rod part 320. The first plunger rod part 318 has a first plunger rod diameter and the second plunger rod part 320 has a second plunger rod diameter. The first plunger rod diameter is larger than the second plunger rod diameter.

When the plunger rod 314 is in a retracted position, as shown in FIG. 6b, the first plunger rod part 318 contacts a surface of the first syringe locking member 368, and the first plunger rod part 318 contacts a surface of the second syringe locking member 370. The first syringe locking member 368 and the second syringe locking member 370 are forced to the second position by the contact with the first plunger rod part 318. Thereby is the syringe lock 366 in the unlocked state.

When the plunger rod 314 is in an advanced position, as shown in FIG. 6a, the second plunger rod part 320 is near the surface of the first syringe locking member 368 and the surface of the second syringe locking member 370. The second plunger rod part 320, having a second plunger rod diameter smaller than the first plunger rod diameter, allows the first syringe locking member spring 372 to force the first syringe locking member 368 into the first position, and the second syringe locking member spring 374 to force the first syringe locking member 370 into the first position.

Upon retraction of the plunger rod 314, the syringe lock 366 is brought to the unlocked state. Upon advancement of the plunger rod 314, the syringe lock 366 is brought to the locked state.

Figure 7:
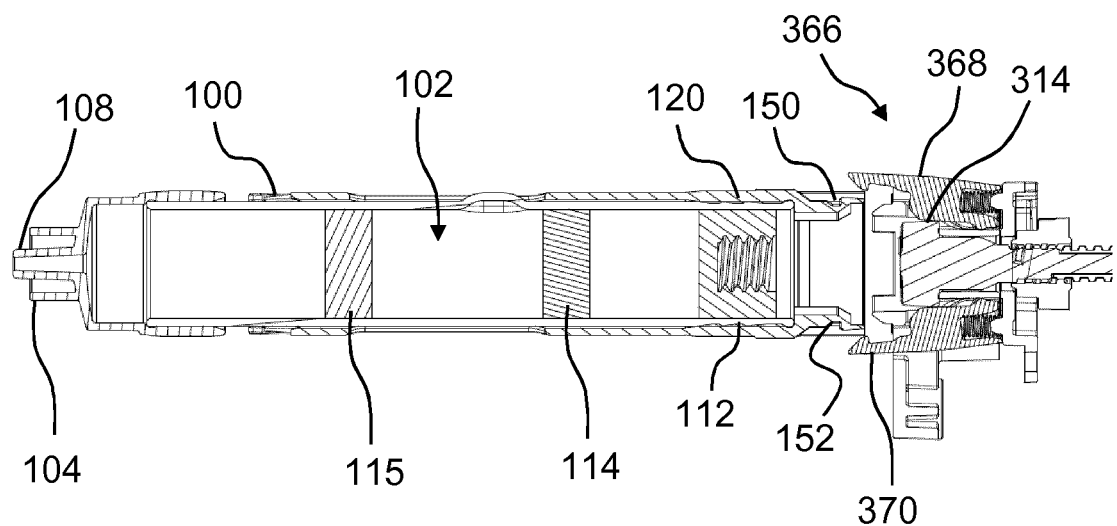
FIG. 7 schematically illustrates an exemplary syringe lock.

FIG. 7 schematically illustrates an exemplary syringe lock 366 engaging and/or releasing a syringe 100.

The plunger rod 314 is in a retracted position. The syringe lock 366 is in the unlocked position. The first syringe locking member 368 and the second syringe locking member 370 are in the first position.

The syringe 100 comprises a compartment 102 configured for containing a medicament. The syringe 100 has a first syringe end 104 and a syringe opening 108 at the first syringe end 104. The syringe 100 is configured to expel medicament through the syringe opening 108. The syringe comprises a first stopper 112, a second stopper 114 and a third stopper 115. The first stopper 112, the second stopper 114, and the third stopper 115 are movable inside the compartment 102.

The syringe 100 comprises a first syringe lock receiver 150 and a second syringe lock receiver 152. The first syringe lock receiver 150 is configured for engagement with the first syringe locking member 368. The second syringe lock receiver 152 is configured for engagement with the second syringe locking member 370. The first syringe lock receiver 150 and/or the second syringe lock receiver 152 may be formed in an outer compartment wall 120 of the compartment 102. Alternatively or additionally, the first syringe lock receiver 150 and/or the second syringe lock receiver 152 may be formed in a syringe lock body attached to compartment wall 120. For example, the first syringe lock receiver 150 and/or the second syringe lock receiver 152 may be formed in an external body fixedly attached to the compartment 102, such as a part of syringe casing as described in relation to other figures, e.g. an inner body of a syringe casing.

Figure 8:
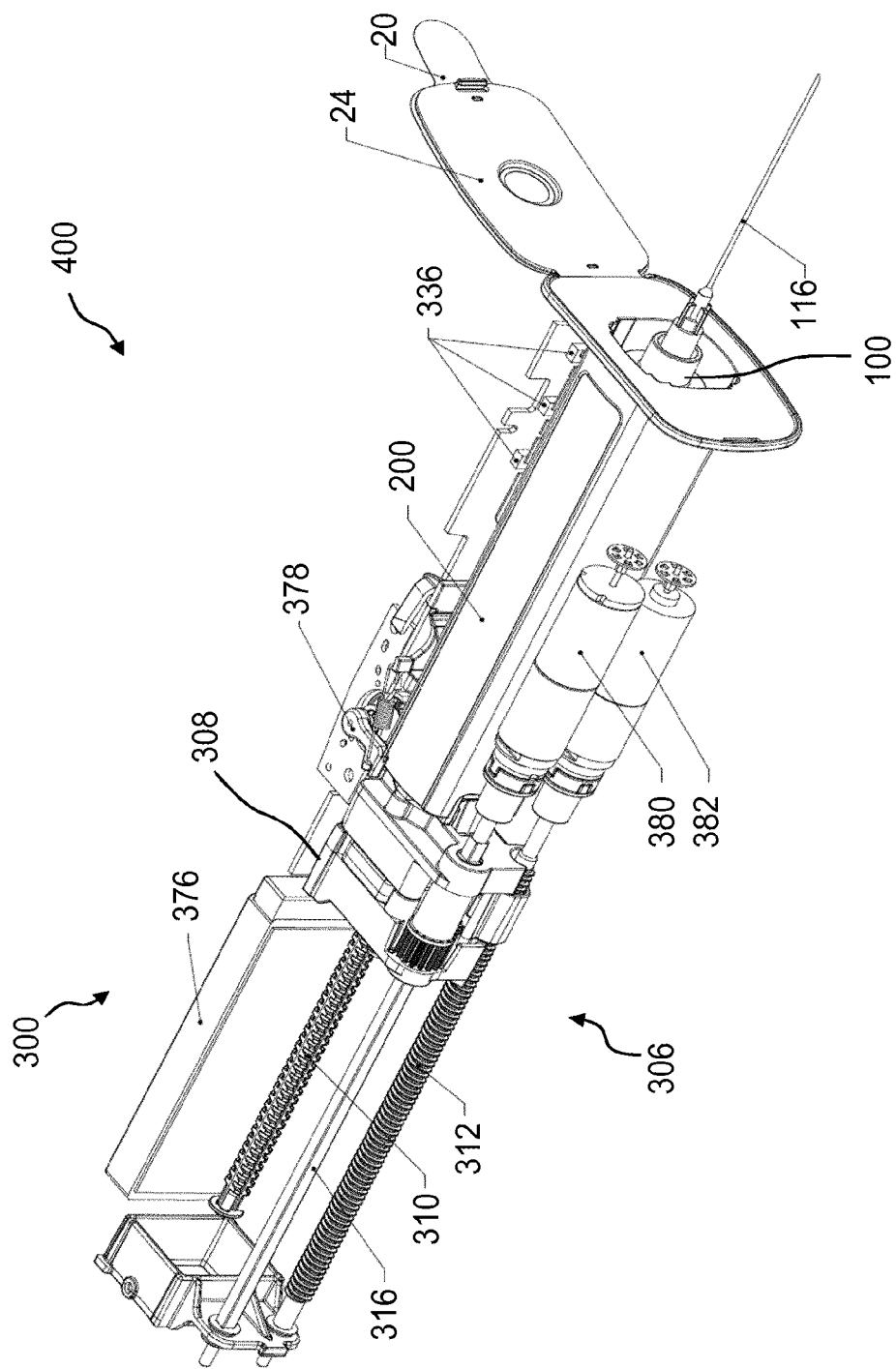
FIG. 8 schematically illustrates an exemplary system.

FIG. 8 schematically illustrates an exemplary system 400 comprising an auto injector 300 and a cartridge 200. The cartridge 200 comprises a syringe 100. The auto injector 300 is shown with outer parts, such as the housing, removed, to allow visibility of internal components of the auto injector 300. In the example illustrated, the cartridge 200 is received in the receiving part of the auto injector 300. The auto injector 300 comprises an operational module 306.

The operational module 306 comprises a stopper operational part 310 configured for moving a stopper of the syringe 100, such as a first stopper of the syringe 100. For example, the first stopper of the syringe may be advanced to expel the medicament of the syringe, e.g. to inject the medicament into tissue of a patient, and/or the first stopper may be advanced to combine two or more medicament components, such as a first medicament component and a second medicament component.

The operational module 306 comprises a syringe operational part 312 configured for moving the syringe 100. For example, the syringe operational part 312 may be configured for advancing the needle 116, e.g. to insert the needle into tissue of a patient, and/or to retract the needle 116 after injection of the medicament, and/or the syringe operational part 312 may be configured for moving the syringe 100 back and forth in order to mix two or more medicament components, such as a first medicament component and a second medicament component, e.g. to dissolve a powder component in a liquid component.

The operational module 306 comprises a carrier 308. In the example depicted, the syringe 100 is attached to the carrier 308, and the syringe operational part 312 is configured for moving the syringe 100 by movement of the carrier 308. The syringe 100 may be locked to the carrier 308 by a syringe lock, as described in relation to other figures, when the syringe 100 is received in the receiving part of the auto injector 300. The syringe lock may have a locked state and an unlocked state, and the syringe lock may be configured to lock the syringe 100 to the carrier 308 in the locked state.

The operational module 306 comprises one or more drivers, such as a stopper driver 380 and a syringe driver 382. The stopper driver 380 is configured to drive the stopper operational part 310, e.g. via a drive axle 316. The drive axle 316 provides that the stopper driver 380 may drive the stopper operational part 310 in all positions of the carrier 308. In an alternative embodiment, the stopper driver 380 may be positioned on the carrier 308, reducing the need for a drive axle 316. The syringe driver 380 is configured to drive the syringe operational part 312, such as to move the carrier 308 and/or the syringe 100.

The stopper driver 380 and/or the syringe driver 382 may be DC motors, e.g. DC motors with or without brushes, e.g. the stopper driver 380 may be a brushed DC motor and/or the syringe driver 382 may be a brushless DC motor. A brushless DC motor may be preferred due to higher durability of a brushless DC motor. Especially for the syringe driver 382 a brushless DC motor may be preferred due to many and/or rapid movements performed by the syringe driver 382.

The auto injector 300 comprises sensors, such as an optical sensor 336. In the depicted example, the auto injector 300 comprises a plurality of optical sensors 336. The optical sensor(s) 336 may be configured for detecting medicament and/or blood in a channel, such as the needle chamber. The optical sensor(s) 336 may be configured for reading an optical code of the cartridge 200, such as an information code of the cartridge 200. A plurality of optical sensors 336, as shown, may provide the possibility of optical reading and/or detection for different positions of the syringe 100.

The auto injector 300 comprises a power unit 376, such as a battery, such as a rechargeable battery, such as a lithium-ion battery. The power unit 376 may supply power to electronic components of the auto injector, e.g. the stopper driver 380, the syringe driver 382, a processing unit, a memory, sensors, such as the optical sensor(s) 336, a user interface, etc.

The auto injector 300 comprises a contact switch 378. The contact switch 378 may provide a signal indicative of the cartridge 200 being inserted in the auto injector 300, e.g. of the cartridge 200 being received in the receiving part of the auto injector 300. Additionally or alternatively, the contact switch 378 may provide a signal indicative of the cartridge 200 and/or the syringe 100 being pressed against a user's skin, e.g. a patient's skin. Thus, the contact switch 378 may be a skin sensor.

The cartridge 200 comprises a cover element 24. The cover element 24 is movable between a first position, as illustrated, and a second position. In the second position, the cover element covers at least a portion of the front end opening, and thereby reduces the front end opening, in order to provide protection of the needle 116, when the syringe 100 is retracted, such that the needle 116 is enclosed inside the cartridge 200.

The cartridge 200 comprises a removable sheet 20. The removable sheet 20 covers the front surface and is configured for removal before abutment of the front end to a user's skin, e.g. a patient's skin. The removable sheet 20 may ensure that a front surface of the front end is maintained sterile until removal of the removable sheet 20, thereby reducing the risk of infection, e.g. infection carried from an operator of the device to the patient.

FIG. 9a-g shows an exemplary step by step procedure of mixing a first medicament component 128 and a second medicament component 130 in a syringe 100.

The syringe 100 comprises a compartment 102 containing a medicament 126. The medicament 126 comprises a first medicament component 128 and a second medicament component 130. The syringe 100 has a first syringe end 104 and a second syringe end 106. The syringe 100 has a syringe opening 108 for fluid communication with the compartment 102 at the first syringe end 104. The syringe 100 comprises an optional syringe channel 110 between the syringe opening 108 and the compartment 102. The syringe 100 is configured to expel the medicament 126 through the syringe channel 110 and the syringe opening 108.

The syringe 100 comprises a first stopper 112 movable inside the compartment 102. The first stopper 112 is movable in a first stopper direction from the second syringe end 106 towards the first syringe end 104.

The syringe 100, as depicted, furthermore comprises a second stopper 114 between the first syringe end 104 and the first stopper 112. The second stopper 114 is movable inside the compartment 102. The second stopper 114 is movable in the first stopper direction. The second stopper divides the compartment 102 into a first compartment part 134 and a second compartment part 136. The first compartment part 134 contains the first medicament component 128. The second compartment part 136 contains the second medicament component 130.

The syringe 100, as depicted, furthermore comprises an optional third stopper 115 between the first syringe end 104 and the second stopper 114. The third stopper 115 is movable inside the compartment 102. The third stopper 115 is movable in the first stopper direction.

The syringe 100 is attached to a carrier 308, such as a carrier 308 of an auto injector. A plunger rod 314 is configured for moving the first stopper 112 at least in the first stopper direction.

Figure 9:
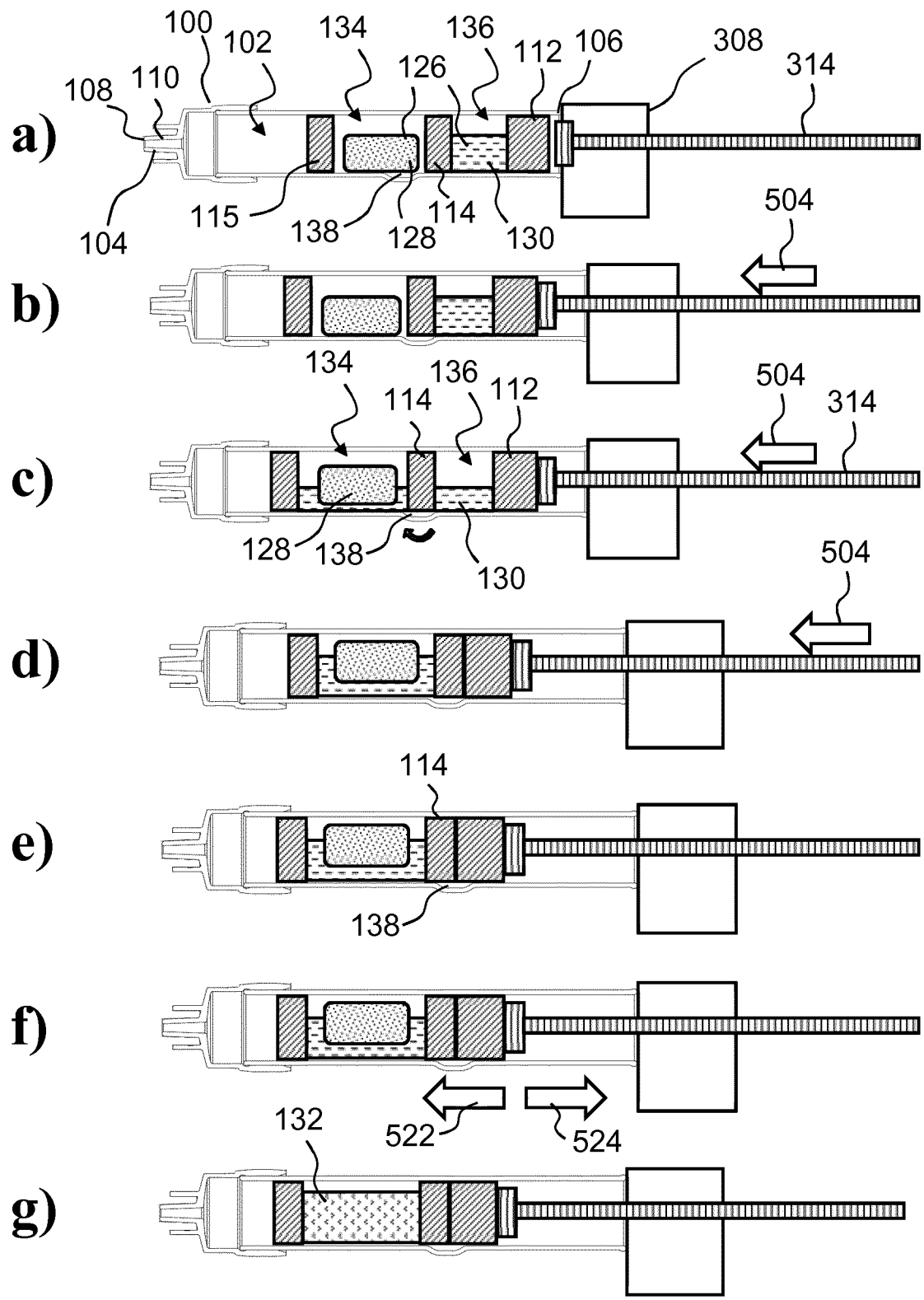
FIG. 9 a-g show an exemplary step by step procedure of mixing.

FIG. 9a shows that the first medicament component 128 and the second medicament component 130 is separated by the second stopper 114. This may illustrate a syringe 100 which is readily received in an auto injector.

FIG. 9b shows that the plunger rod 314 moves forward, e.g. in the first stopper direction. The plunger rod 314 moves the first stopper 112 in the first stopper direction. The movement of the first stopper 112 in the first stopper direction causes the second stopper 114 to move in the first stopper direction. The movement of the first stopper 112 in the first stopper direction may cause increased pressure inside the second compartment part, the increased pressure may cause movement of the second stopper 114 in the first stopper direction. Especially, in situations where the substance in the second compartment part 136, e.g. the second medicament component 130, is practically incompressible, such as a liquid, movement of the first stopper 112 in the first stopper direction may cause movement of the second stopper 114 in the first stopper direction.

The second stopper 114 is moved to be positioned in the middle bypass section 138. Thereby bringing the first compartment part 134 in fluid communication with the second compartment part 136.

FIG. 9c shows that the plunger rod 314 continue movement of the first stopper 112 in the first stopper direction. The second stopper 114 is positioned in the middle bypass section. The first compartment part 134 is in fluid communication with the second compartment part 136 through the middle bypass section 138. The continued movement of plunger rod 314 and the first stopper 112 in the first stopper direction cause the second medicament component 130 to be transferred from the second compartment part 136 to the first compartment part 134 through the middle bypass section 138. The first medicament component 128 and the second medicament component 130 are being combined in first compartment part 134. It may be preferred that the transfer of liquid through the middle bypass section 138 happens at a low speed, e.g. the plunger rod 314 may provide a movement in the first stopper direction between 1-4 mm/s, such as 2 mm/s.

FIG. 9d shows that the first stopper 112 has been moved a first stopper distance by the plunger rod 314. The first stopper distance positions the first stopper 112 in adjacent with the second stopper 114, such as in contact with the second stopper 114. The first medicament component 128 and the second medicament component 130 are combined in first compartment part 134.

FIG. 9e shows that the first stopper 112 and the second stopper 114 has been further moved by the plunger rod 314, such that the second stopper 114 is moved out of the middle bypass section, e.g. beyond the middle bypass section, closing the fluid connection through the middle bypass section.

FIG. 9f shows that the syringe 100 is moved in a first mixing direction 522 and in a second mixing direction 524. For example, the syringe may be moved alternatingly in the first mixing direction 522 and in the second mixing direction 524. The mixing movement 522, 524 is provided to mix the first medicament component 128 and the second medicament component 130. The syringe 100 may be moved by moving the carrier 308 in the first mixing direction 522 and in the second mixing direction 524. As illustrated, the first mixing direction 522 and/or the second mixing direction 524 may be parallel to the first stopper direction 504. The syringe 100 and the carrier 308 may be moved in the first mixing direction 522 and the second mixing direction 524 for a predetermined duration of time.

FIG. 9g shows that the first medicament component 128 and the second medicament component 130 have been mixed to obtain a mixed medicament 132, e.g. after movement of the syringe 100 and the carrier 308 in the first mixing direction 522 and the second mixing direction 524 for a predetermined duration of time. The mixed medicament 132 may be injected into the tissue of a patient.

Expelling of the mixed medicament 132 through the syringe opening 108 may be achieved by the plunger rod 314 further moving the first stopper 112 in the first stopper direction 504. Movement of the first stopper 112 in the first stopper direction causes the second stopper 114 and the third stopper 115 to move in the first stopper direction, and expelling of the mixed medicament 132.

Figure 10:
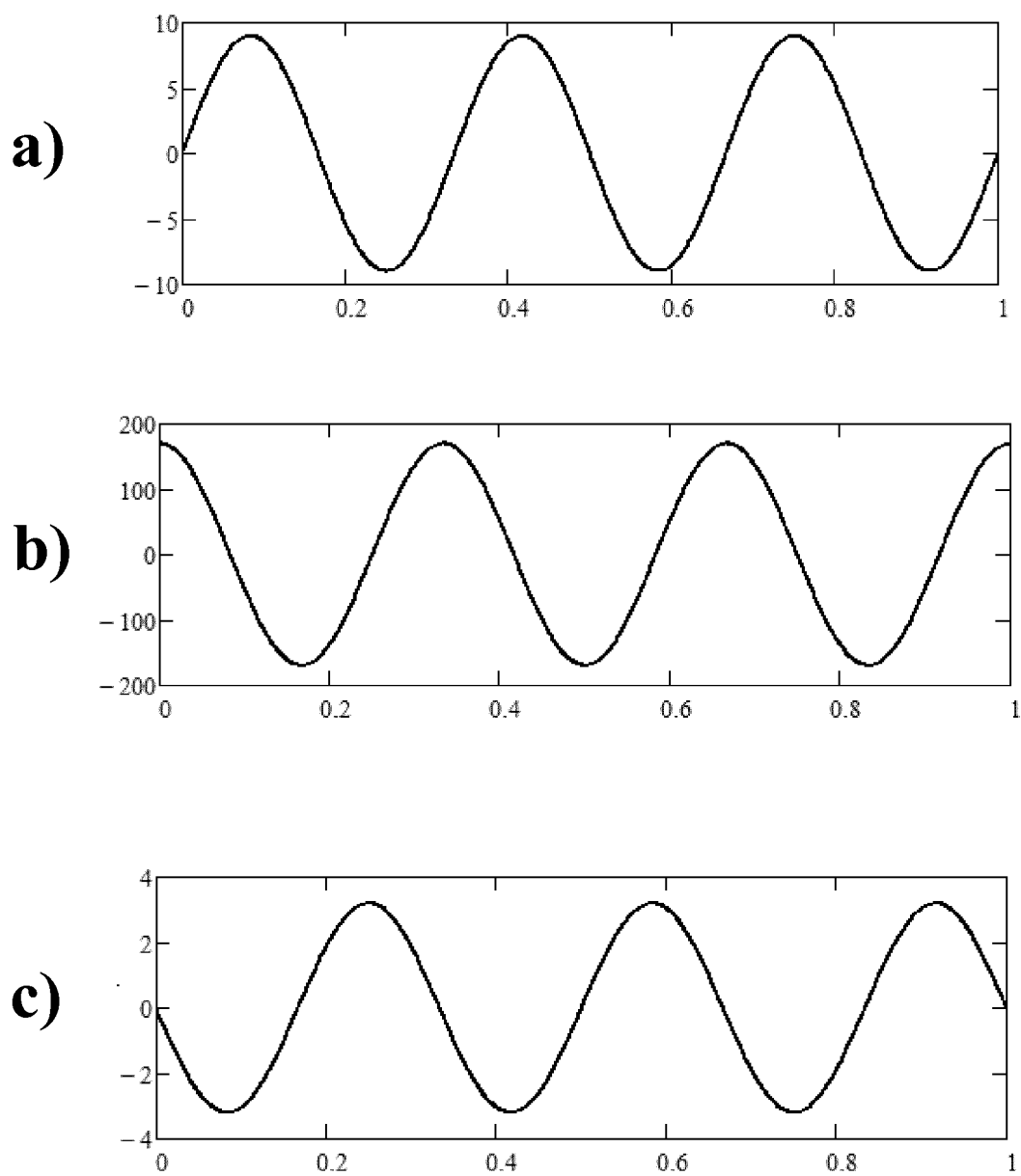
FIG. 10 a-c show time varying profiles of an exemplary mixing movement.

FIG. 10a-c show time varying profiles of an exemplary mixing movement, such as a mixing movement as described in relation to other figures, such as profiles of movements of a syringe and/or a carrier attached to a syringe, wherein a first medicament component is mixed with a second medicament component to obtain a mixed medicament component. The horizontal axes denotes time in seconds. The illustrated mixing movement is a periodic movement, wherein the position profile, the velocity profile and the acceleration profile resembles sine waves.

FIG. 10a shows a time varying position profile of the syringe relative to a center position, such as a starting position, e.g. relative to an auto injector performing the movement of the syringe, such as relative to a housing of the auto injector. The vertical axis denotes the position in mm from the center position, such as the starting position. Positive position denotes movement away from the center position in a first mixing direction. Negative position denotes movement away from the center position in a second mixing direction.

FIG. 10b shows a time varying velocity profile of the syringe, e.g. relative to the auto injector performing the movement of the syringe, such as relative to a housing of the auto injector. The vertical axis denotes the velocity in mm/s. Positive velocity denotes movement in the first mixing direction. Negative velocity denotes movement in the second mixing direction. The time varying velocity profile is varying periodically over time, e.g. resembling a sine wave.

The time varying velocity profile has a first maximum velocity in the first mixing direction and a second maximum velocity in the second mixing direction. The first and/or second maximum velocity may be represented by their absolute value(s). The first maximum velocity and the second maximum velocity are larger than 50 mm/s, such as larger than 100 mm/s, such as larger than 150 mm/s, such as 180 mm/s.

FIG. 10c shows a time varying acceleration profile of the syringe, e.g. relative to the auto injector performing the movement of the syringe, such as relative to a housing of the auto injector. The vertical axis denotes the acceleration in $m/s^2$. Positive acceleration denotes acceleration in the first mixing direction. Negative acceleration denotes acceleration in the second mixing direction.

The time varying acceleration profile has a first maximum acceleration in the first mixing direction and a second maximum acceleration in the second mixing direction. The first and/or second maximum acceleration(s) may be represented by their absolute value(s). The first maximum acceleration and the second maximum acceleration are larger than 2 $m/s^2$, such as larger than 3 $m/s^2$, such as 3.2 $m/s^2$.

Figure 11:
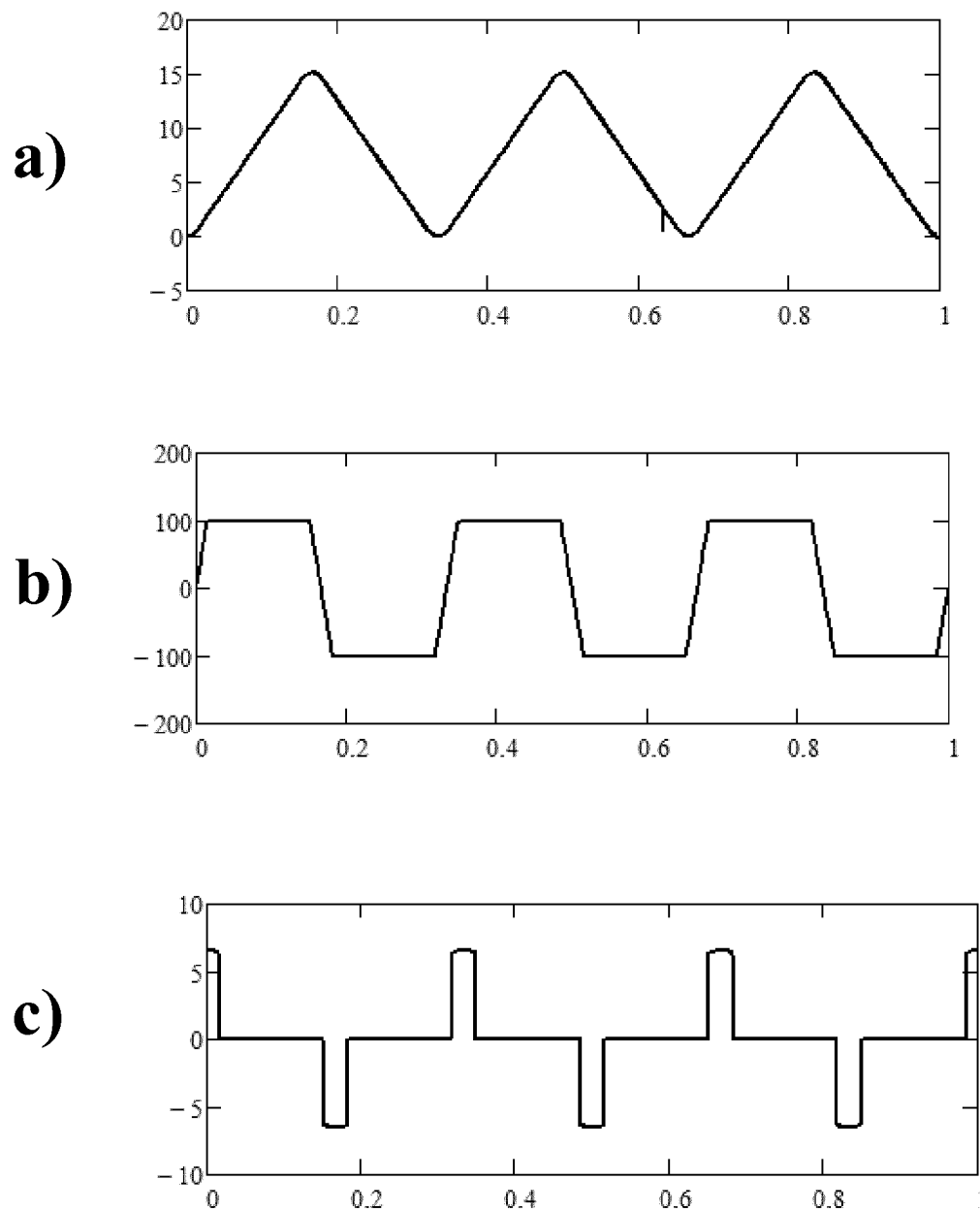
FIG. 11 a-c show time varying profiles of an exemplary mixing movement.

FIG. 11a-c show time varying profiles of an exemplary mixing movement, such as a mixing movement as described in relation to other figures, such as profiles of movements of a syringe and/or a carrier attached to a syringe, wherein a first medicament component is mixed with a second medicament component to obtain a mixed medicament component. The horizontal axes denotes time in seconds. The illustrated mixing movement is a periodic movement.

FIG. 11a shows a time varying position profile of the syringe relative to a center position, such as a starting position, e.g. relative to an auto injector performing the movement of the syringe, such as relative to a housing of the auto injector. The vertical axis denotes the position in mm from the center position, such as the starting position. The time varying position profile resembles a sawtooth wave. Positive position denotes movement away from the center position in a first mixing direction. Negative position denotes movement away from the center position in a second mixing direction. The time varying position profile shows that the syringe and/or carrier is moved 15 mm in the first mixing direction, thereafter, the syringe and/or carrier is moved 15 mm in the second mixing direction, thereby the syringe and/or carrier is back to the starting position.

FIG. 11b shows a time varying velocity profile of the syringe, e.g. relative to the auto injector performing the movement of the syringe, such as relative to a housing of the auto injector. The vertical axis denotes the velocity in mm/s. Positive velocity denotes movement in the first mixing direction. Negative velocity denotes movement in the second mixing direction. The time varying velocity profile is varying periodically over time, e.g. resembling a trapezoid wave.

The time varying velocity profile has a first maximum velocity in the first mixing direction and a second maximum velocity in the second mixing direction. The first maximum velocity is a first constant velocity, and the second maximum velocity is a second constant velocity. The first and/or second constant velocity may be a velocity maintained for at least 0.1 seconds, such as 0.15 seconds. The first and/or second maximum velocity may be represented by their absolute value(s). The first maximum velocity and the second maximum velocity are larger than 50 mm/s, such 100 mm/s.

In this example, the first maximum velocity and the second maximum velocity are of equal magnitude. However, in other exemplary mixing movements, the first maximum velocity and the second maximum velocity may be of different magnitude, e.g. the first maximum velocity may be of greater magnitude than the second maximum velocity.

FIG. 11c shows a time varying acceleration profile of the syringe and/or carrier, e.g. relative to the auto injector performing the movement of the syringe, such as relative to a housing of the auto injector. The vertical axis denotes the acceleration in $m/s^2$. Positive acceleration denotes acceleration in the first mixing direction. Negative acceleration denotes acceleration in the second mixing direction.

The time varying acceleration profile has a first maximum acceleration in the first mixing direction and a second maximum acceleration in the second mixing direction. The first and/or second maximum acceleration(s) may be represented by their absolute value(s). The first maximum acceleration and the second maximum acceleration are larger than 2 $m/s^2$, such as larger than 4 $m/s^2$, such as 5.2 $m/s^2$.

The time varying acceleration profile have periods where the acceleration is zero. The time varying velocity profile have periods where the velocity is constant. The time varying position profile have periods following a straight curve.

Figure 12:
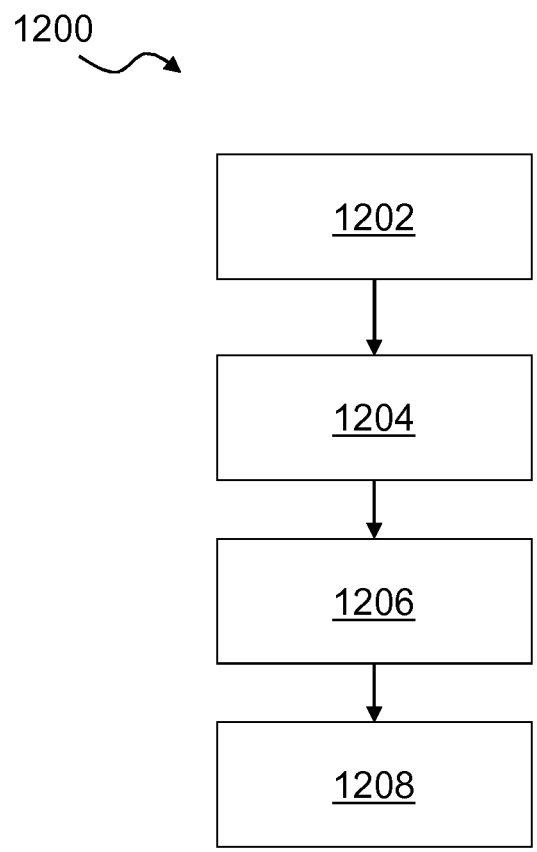
FIG. 12 shows a flow diagram of an exemplary method.

FIG. 12 shows a flow diagram of an exemplary method 1200 for administering injection of a medicament, such as a medicament comprising a first medicament component and a second medicament component.

The method 1200 comprises moving 1202 a first stopper of the syringe a first stopper distance to combine the first medicament component and the second medicament component. The first medicament component and the second medicament component may be combined in a compartment and/or a compartment part, such as a first compartment part. Moving 1202 the first stopper may comprise moving the first stopper in a first stopper direction along a stopper axis. Moving 1202 the first stopper may be performed by operation of the operational module, such as a stopper operational part of the operational module.

The method 1200 comprises moving 1204 the syringe to obtain a mixed medicament, e.g. a medicament wherein the first medicament component is dissolved in the second medicament component, and/or wherein the first medicament component is suspended and/or distributed in the second medicament component.

The movement 1204 of the syringe may have a time varying acceleration profile having a first maximum acceleration in a first mixing direction and a second maximum acceleration in a second mixing direction. The first maximum acceleration and/or the second maximum acceleration may be larger than a predetermined acceleration threshold, e.g. larger than 2 m/s$^2$. Moving 1204 the syringe may be performed by operation of the operational module, such as a syringe operational part of the operational module.

The movement 1204 of the syringe may be a reciprocating movement, and/or an alternating movement, such as a movement in the first mixing direction followed by a movement in the second mixing direction, followed by a movement in the first mixing direction, and so forth. For example, the movement 1204 of the syringe may comprise moving the syringe for a predetermined duration.

The method 1200 comprises moving 1206 the syringe to advance a needle of the syringe, and/or a needle attached to the syringe. For example, the needle may be advanced to penetrate the skin of a patient and to be inserted into the tissue of the patient.

The method 1200 comprises moving 1208 the first stopper of the syringe in the first stopper direction to expel the mixed medicament through a syringe opening of the syringe, and/or to expel the mixed medicament through the needle of syringe and/or through a needle attached to the syringe. Moving 1208 the first stopper may be performed by operation of the operational module, such as the stopper operational part of the operational module.

In some exemplary methods, one or more of the steps as illustrated, may be omitted. For example another exemplary method may comprise the step of moving the syringe to mix the first medicament component and the second medicament component to obtain a mixed medicament.

Figure 13:
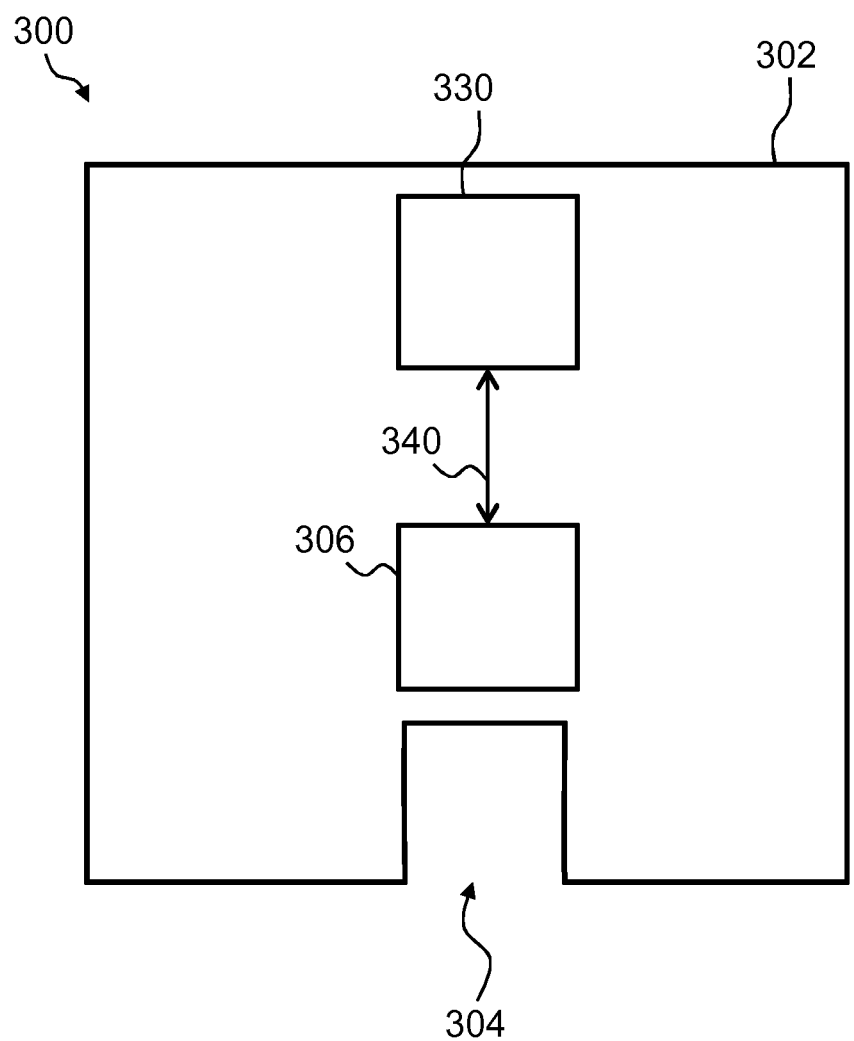
FIG. 13 schematically illustrates an exemplary auto injector.

FIG. 13 schematically illustrates an exemplary auto injector 300, such as an auto injector for administering injection of a medicament, such as an auto injector as described in relation to other figures. The auto injector 300 comprises a housing 302, a receiving part 304, an operational module 306, and a processing unit 330.

The receiving part 304 is configured for receiving a syringe containing the medicament. The receiving part 304 may be configured for receiving a cartridge comprising the syringe.

The operational module 306 is configured for interacting with the syringe and/or the cartridge, e.g. when the syringe and/or the cartridge are received in the receiving part 304. The operational module 306 is configured for moving a first stopper of the syringe at least in a first stopper direction, e.g. to expel medicament through a first syringe channel of the syringe and/or through a syringe opening. The syringe may comprise a second stopper and/or a third stopper, and the operational module 306 may be configured for moving the second stopper and/or the third stopper, e.g. to expel medicament through the first syringe channel and/or through a syringe opening.

The processing unit 330 is configured to provide a control signal 340 to the operational module 306. For example, the control signal 340 may be configured to cause the operational module 306 to move the first stopper in the first stopper direction. Alternatively or additionally, the control signal 340 may be configured to cause the operational module to move the syringe in a first mixing direction and/or in a second mixing direction.

Control of the operational module 306 may comprise activation and/or deactivation of the operational module 306, and/or parts of the operational module 306, such as a syringe operational part and/or a stopper operational part, as described in relation to other figures.

The processing unit 330 may be configured to operate the operational module, and/or one or more parts of the operational module, such as a syringe operational part and/or a stopper operational part, in accordance with the method 1200, or parts of the method 1200 as described in relation to other figures.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES 2 syringe casing
4 main body
6 tube part
8 tube part outer perimeter
10 front end
12 front end opening
14 front end outer perimeter
16 inner body
18 locking element
20 removable sheet
22 front surface
24 cover element
26 cover part
28 cover opening
40 cover surface
100 syringe
102 compartment
104 first syringe end
106 second syringe end
108 syringe opening
110 first syringe channel
112 first stopper
114 second stopper
115 third stopper
116 needle
120 outer compartment wall
124 needle tip
126 medicament
128 first medicament component
130 second medicament component
132 mixed medicament
134 first compartment part
136 second compartment part
138 middle bypass section
139 front bypass section
140 syringe cap
150 first syringe lock receiver
152 second syringe lock receiver
200 cartridge
300 auto injector
302 housing
304 receiving part
306 operational module
308 carrier 310 stopper operational part
312 syringe operational part
314 plunger rod
316 drive axle
318 first plunger rod part
320 second plunger rod part
336 optical sensor
350 display unit
354 housing front part
356 housing front part outer perimeter
358 user interface
366 syringe lock
368 first syringe locking member
370 second syringe locking member
372 first syringe locking member spring
374 second syringe locking member spring
376 power unit
378 contact switch
380 stopper driver
382 syringe driver
400 system
500 tube axis
502, 504, 505 first stopper direction
503 second stopper direction
512 stopper axis
522 first mixing direction/first syringe direction
524 second mixing direction/second syringe direction
530 syringe axis
1200 method for administering injection of a medicament
1202 moving a first stopper of the syringe a first stopper distance
1204 moving the syringe to obtain a mixed medicament
1206 moving the syringe to advance a needle
1208 moving first stopper to expel the mixed medicament

The invention claimed is:

1. An auto injector for administering injection of a medicament comprising a first medicament component and a second medicament component, the auto injector comprising:
a housing;
a receiving part configured for receiving a syringe containing the medicament;
an operational module configured for interacting with the syringe, the operational module comprising a carrier for attaching to the syringe and a syringe operational part, which is configured to move the carrier in a first mixing direction and in a second mixing direction which is opposite to the first mixing direction; and
a processing unit connected to the syringe operational part, wherein the processing unit is programmed to:
control the syringe operational part to alternately move the carrier in the first mixing direction and in the second mixing direction to mix the first medicament component and the second medicament component to obtain a mixed medicament,
wherein the movement of the carrier in the first mixing direction and in the second mixing direction has a time varying acceleration profile, the time varying acceleration profile having a first maximum acceleration in the first mixing direction and a second maximum acceleration in the second mixing direction, and wherein the first maximum acceleration or the second maximum acceleration is larger than a predetermined acceleration threshold,
wherein the movement of the carrier in the first mixing direction and in the second mixing direction has a time varying velocity profile, the time varying velocity profile varying periodically over time, wherein the time varying velocity profile resembles a wave, and wherein the processing unit is configured to move the carrier to obtain at least two velocity wave profiles selected from the group consisting of a sine wave, a trapezoid wave, a sawtooth wave, a rectangular wave, and a triangular wave, and wherein one of the at least two velocity wave profiles is selected from the group consisting of the sine wave, the trapezoid wave, the sawtooth wave, and the triangular wave.

2. The auto injector according to claim 1, wherein the predetermined acceleration threshold is larger than 2 m/s$^2$.

3. The auto injector according to claim 1, wherein controlling the syringe operational part comprises moving the carrier for a predetermined duration of time.

4. The auto injector according to claim 1, wherein the operational module comprises a stopper operational part configured to move a first stopper of the syringe at least in a first stopper direction along a stopper axis, and wherein the processing unit is connected to the stopper operational part.

5. The auto injector according to claim 4, wherein the processing unit is configured to operate the stopper operational part to move the first stopper a distance in the first stopper direction to combine the first medicament component and the second medicament component.

6. The auto injector according to claim 4, wherein the processing unit is configured to operate the stopper operational part to move the first stopper in the first stopper direction to expel the mixed medicament through a syringe opening.

7. The auto injector according to claim 4, wherein the first mixing direction is along the stopper axis.

8. The auto injector according to claim 1, wherein the processing unit is configured to operate the syringe operational part to advance a needle attached to the syringe.

9. The auto injector according to claim 1, wherein the operational module comprises a syringe lock having a locked state and an unlocked state, and wherein the syringe lock is configured to lock the syringe to the carrier in the locked state.

10. The auto injector according to claim 9, wherein the syringe lock comprises a first syringe locking member, the first syringe locking member being in a first position when the syringe lock is in the locked state, and the first syringe locking member being in a second position when the syringe lock is in the unlocked state.

11. The auto injector according to claim 10, wherein the first syringe locking member is biased towards the first position.

12. The auto injector according to claim 10, wherein the first syringe locking member is configured to be forced to the second position by a predefined movement of a plunger rod of the operational module.

13. An auto injector for administering injection of a medicament comprising a first medicament component and a second medicament component, the auto injector comprising:
a housing;
a receiving part configured for receiving a syringe containing the medicament;
an operational module configured for interacting with the syringe, the operational module comprising a carrier for attaching to the syringe and a syringe operational part, which is configured to move the carrier in a first mixing direction and in a second mixing direction which is opposite to the first mixing direction; and a processing unit connected to the syringe operational part, wherein the processing unit is programmed to:

control the syringe operational part to alternately move the carrier in the first mixing direction and in the second mixing direction to mix the first medicament component and the second medicament component to obtain a mixed medicament, wherein the movement of the carrier in the first mixing direction and in the second mixing direction has a time varying acceleration profile, the time varying acceleration profile having a first maximum acceleration in the first mixing direction and a second maximum acceleration in the second mixing direction, and wherein the first maximum acceleration or the second maximum acceleration is larger than a predetermined acceleration threshold, wherein the movement of the carrier in the first mixing direction and in the second mixing direction has a time varying velocity profile, the time varying velocity profile varying periodically over time, wherein the time varying velocity profile is selected from the group consisting of a sine wave, a trapezoid wave, a sawtooth wave, and a triangular wave.

14. An auto injector for administering injection of a medicament comprising a first medicament component and a second medicament component, the auto injector comprising:

a housing;

a receiving part configured for receiving a syringe containing the medicament;

an operational module configured for interacting with the syringe, the operational module comprising a carrier for attaching to the syringe and a syringe operational part, which is configured to move the carrier in a first mixing direction and in a second mixing direction which is opposite to the first mixing direction; and a processing unit connected to the syringe operational part, wherein the processing unit is programmed to control the syringe operational part to alternately move the carrier in the first mixing direction and in the second mixing direction along a programmed path in predetermined patterns of movement to mix the first medicament component and the second medicament component to obtain a mixed medicament, wherein the movement of the carrier in the first mixing direction and in the second mixing direction has a time varying acceleration profile, the time varying acceleration profile having a first maximum acceleration in the first mixing direction and a second maximum acceleration in the second mixing direction, and wherein the first maximum acceleration or the second maximum acceleration is larger than a predetermined acceleration threshold, wherein the time varying acceleration profile is selected from the group consisting of a sine wave, a trapezoid wave, a sawtooth wave, and a triangular wave.

15. The auto injector according to claim 14, wherein the movement of the carrier in the first mixing direction and in the second mixing direction has a time varying velocity profile, the time varying velocity profile varying periodically over time.

16. The auto injector according to claim 15, the time varying velocity profile having a first maximum velocity in the first mixing direction and a second maximum velocity in the second mixing direction.

17. The auto injector according to claim 16, wherein the first maximum velocity or the second maximum velocity is more than a predetermined velocity threshold.

18. The auto injector according to claim 15, wherein the time varying velocity profile resembles a sine wave, a trapezoid wave, a sawtooth wave, a rectangular wave, or a triangular wave.

* * * * *